United States Patent [19]

Baker et al.

[11] Patent Number: 4,927,819
[45] Date of Patent: May 22, 1990

[54] CYCLO-OCTANE NEUROPROTECTIVE AGENTS

[75] Inventors: Raymond Baker, Much Hadham; William R. Carling, Bishops Stortford; Kim James, Welwyn Garden City; Paul D. Leeson, Cambridge, all of England

[73] Assignee: Merck Sharp & Dohme Limited, Hoddesdon, England

[21] Appl. No.: 274,436

[22] Filed: Nov. 22, 1988

[30] Foreign Application Priority Data

Nov. 30, 1987 [GB] United Kingdom ............... 8727989

[51] Int. Cl.$^5$ ................ A61K 31/435; C07D 225/08
[52] U.S. Cl. .................................. 514/213; 540/521; 540/581
[58] Field of Search ................ 540/581, 521; 514/213

[56] References Cited

U.S. PATENT DOCUMENTS 4,414,154 11/1983 Anderson et al. ............... 260/245.7

FOREIGN PATENT DOCUMENTS 0230370 1/1987 European Pat. Off. .

Primary Examiner—Mukund J. Shah
Assistant Examiner—E. C. Ward
Attorney, Agent, or Firm—William H. Nicholson; Joseph F. DePrima

[57] ABSTRACT

The present invention provides a compound of formula I:

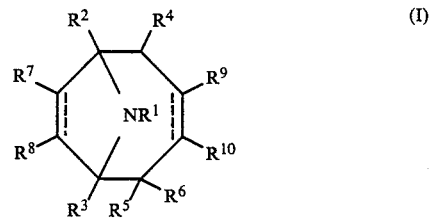

or a salt thereof, wherein:
  the dotted lines represent optional double bonds;
  $R^1$ represents hydrogen, hydroxy, alkenyl, alkyl, aminoalkyl or hydroxyalkyl;
  $R^2$, $R^3$, $R^4$, $R^5$ and $R^6$ independently represet hydrogen, hydroxy, fluoro, alkenyl, aryl, alkyl, or alkyl substituted with aryl, amino, hydroxy, carboxy or fluoro; and
  $R^7$, $R^8$, $R^9$ and $R^{10}$ independently represent hydrogen, hydrocarbon or a heterocyclic group provided that $R^7$, $R^8$, $R^9$ and $R^{10}$ are not simultaneously hydrogen; or
  $R^7$ and $R^8$ and/or $R^9$ and $R^{10}$ may complete a saturated or unsaturated $C_{4-9}$ hydrocarbon or heterocyclic ring; which compounds are useful as anticonvulsant agents and in the treatment and/or prevention of neurodegenerative disorders.

9 Claims, No Drawings

CYCLO-OCTANE NEUROPROTECTIVE AGENTS

This invention relates to a class of cyclooctenimine derivatives which are specific antagonists of N-methyl-D-aspartate (NMDA) receptors and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Olivo-ponto-cerebellar atrophy, anoxia such as from drowning, spinal cord injury and poisoning by exogenous NMDA poisons. The compounds are also useful as anticonvulsant agents.

Certain dibenzocyclooctenimines are disclosed in U.S. Pat. No. 4,414,154, and British Patent No. 2,004,550, and the use of those compounds in the treatment of neurodegenerative diseases is described in published European Patent application No. 230,370. The prior art compounds are dibenzo[a,d]cyclooctenimine derivatives.

The cyclooctenimines of this invention comprise either a dibenzo[a,e]cyclooctenimine moiety, cyclooctenimine moiety, which represents a novel ring system, or they possess no fused benzo ring. The cyclooctenimines of this invention, including dibenzo derivatives thereof, have been found to be highly potent non-competitive centrally acting selective NMDA receptor antagonists.

Accordingly, the present invention provides a compound of formula I:

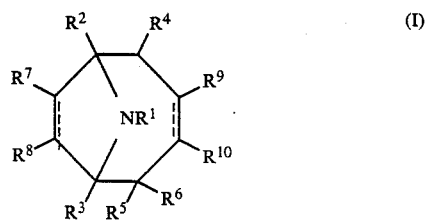

or a salt thereof, wherein:

The dotted lines represent optional double bonds;

$R^1$ represents hydrogen, hydroxy, alkenyl, alkyl, aminoalkyl or hydroxyalkyl;

$R^2$, $R^3$, $R^4$, $R^5$ and $R^6$ independently represent hydrogen, hydroxy, fluoro, alkenyl, aryl, alkyl, or alkyl substituted with aryl, amino, hydroxy, carboxy or fluoro; and $R^7$, $R^8$, $R^9$ and $R^{10}$ independently represent hydrogen, hydrocarbon or a heterocyclic group provided that $R^7$, $R^8$, $R^9$ and $R^{10}$ are not simultaneously hydrogen; or $R^7$ and $R^8$ and/or $R^9$ and $R^{10}$ may complete a saturated or unsaturated $C_{4-9}$ hydrocarbon or heterocyclic ring.

The term 'hydrocarbon' includes groups having up to 18 carbon atoms, suitably up to 10 carbon atoms, conveniently up to 6 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, $C_{5-7}$ cycloalkenyl, $C_{5-7}$ cycloalkenyl($C_{1-6}$)alkyl, aryl and aryl($C_{1-6}$)alkyl.

Suitable alkyl groups include straight and branched chain alkyl groups containing from 1 to 6 carbon atoms, such as methyl, ethyl, propyl and butyl.

When used herein the term 'aryl' includes optionally substituted phenyl and naphthyl.

Suitable alkenyl groups are $C_{2-6}$ alkenyl, such as ethenyl.

The term 'heterocyclic' includes single or fused rings comprising up to four hetero atoms in the ring selected from oxygen, nitrogen and sulphur. Suitable heterocyclic groups include pyridyl, thienyl, furyl, indolyl, benzothienyl, benzofuryl and quinolinyl.

Any of the hydrocarbon or heterocyclic groups may be substituted with a group selected from halogen, $C_{1-6}$ alkyl, aryl, arylalkyl, $C_{1-6}$ alkoxy, halo($C_{1-6}$)alkyl, hydroxy, amino, nitro, carboxy, $C_{1-6}$ alkoxycarbonyl, $C_{1-6}$ alkoxycarbonyl($C_{1-6}$)alkyl, $C_{1-6}$ alkylcarbonyloxy and $C_{1-6}$ alkylcarbonyl groups. Preferred substituent groups include halogen, hydroxy, $C_{1-6}$ alkyl and $C_{1-6}$ alkoxy.

Suitable acid addition salts of compounds of this invention include pharmaceutically acceptable inorganic salts such as sulphate, nitrate, phosphate, borate, hydrochloride and hydrobromide, and pharmaceutically acceptable organic acid addition salts such as acetate, tartrate, maleate, citrate, succinate, benzoate, ascorbate, methanesulphonate, α-ketoglutarate, α-glycerophosphate and glucose-1-phosphate. Preferably the acid addition salt is a hemisuccinate, hydrochloride, α-ketoglutarate, α-glycerophosphate, maleate or glucose-1-phosphate, in particular the hydrochloride or maleate salt.

The substituents $R^4$, $R^5$ and $R^6$ may be present in the exo or endo configuration. The present invention includes all such isomers and mixtures thereof. In addition, when a compound of the invention has a chiral centre, all enantiomers and mixtures thereof, including racemic mixtures thereof, are included within the invention.

When $R^7$ and $R^8$ or $R^9$ and $R^{10}$ together represent the residue of a hydrocarbon ring, the ring may be saturated or unsaturated. The $R^7/R^8$ or $R^9/R^{10}$ carbon chain may comprise from 2 to 7 carbon atoms, preferably 3 or 4 carbon atoms, i.e. forming a fused 5 - or 6 -membered ring. Preferably $R^7$ and $R^8$ and also $R^9$ and $R^{10}$ complete optionally substituted benzo or cyclohexane rings.

Preferred values for the substituent $R^1$ are hydrogen and $C_{1-4}$ alkyl.

Preferably $R^2$ to $R^6$ independently represent hydrogen, hydroxy, fluoro or $C_{1-6}$ alkyl, especially hydrogen, hydroxy or $C_{1-4}$ alkyl.

One subgroup of compounds of this invention is represented by formula II:

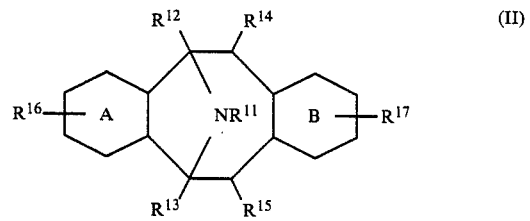

wherein rings A and B independently represent cyclohexane, cyclohexene, cyclohexadiene or benzene rings; $R^{11}$ is as defined above for $R^1$; and $R^{12}$ to $R^{17}$ independently represent hydrogen, hydroxy, $C_{1-6}$ alkyl, aryl, arylalkyl, $C_{1-6}$ alkoxy or halogen.

When the bond common to ring A or ring B and the cyclooctane ring is saturated, each bridgehead position may be in either the exo or the endo configuration. This leads to a maximum of two cis and two trans isomers for each structure. The bridgehead positions are also chiral and therefore will lead to enantiomeric isomers.

Preferably rings A and B represent benzene rings and R16 and R17 independently represent hydrogen, methyl, hydroxy, methoxy, bromo or chloro. Preferably $R^{13}$ is methyl.

Particular compounds of this invention include:
6-methyl-5,6,11,12-tetrahydrodibenzo[a,e]cycloocten6,11-imine;
11-n-butyl-6-methyl-5,6,11,12-tetrahydrodibenzo[a,e]cycloocten-6,11-imine;
5,6-dimethyl-5,6,11,12-tetrahydrodibenzo[a,e]cycloocten-6,11-imine;
2-bromo-6-methyl-5,6,11,12-tetrahydrodibenzo[a,e]cycloocten-6,11-imine;
9-bromo-6-methyl-5,6,11,12-tetrahydrodibenzo[a,e]cycloocten-6,11-imine;
3,6-dimethyl-5,6,11,12-tetrahydrodibenzo[a,e]cycloocten-6,11-imine;
6,8-dimethyl-5,6,11,12-tetrahydrodibenzo[a,e]cycloocten-6,11-imine;
2-chloro-6-methyl-5,6,11,12-tetrahydrodibenzo[a,e]cycloocten-6,11-imine;
9-chloro-6-methyl-5,6,11,12-tetrahydrodibenzo[a,e]cycloocten-6,11-imine;
3-bromo-6-methyl-5,6,11,12-tetrahydrodibenzo[a,e]cycloocten-6,11-imine;
6-methyl-5,6,6a-exo,7,8,9,10,10a-exo,11,12-decahydrodibenzo[a,e]cycloocten-6,11-imine;
6-methyl-5,6,6a-endo,7,8,9,10,10a-endo,11,12-decahydrodibenzo[a,e]cycloocten-6,11-imine;
5,6,11,12 tetrahydrodibenzo[a,e]cycloocten-6,11-imine;
6,11-dimethyl-5,6,11,12-tetrahydrodibenzo[a,e]cycloocten-6,11-imine;
2-methoxy-6-methyl-5,6,11,12-tetrahydrodibenzo[a,e]cycloocten-6,11-imine;
3-methoxy-6-methyl-5,6,11,12-tetrahydrodibenzo[a,e]cycloocten-6,11-imine;
2-hydroxy-6-methyl-5,6,11,12-tetrahydrodibenzo[a,e]cycloocten-6,11-imine;
3-hydroxy-6-methyl-5,6,11,12-tetrahydrodibenzo[a,e]cycloocten-6,11-imine;
12-exo-hydroxy-6-methyl-5,6,11,12-tetrahydrodibenzoa,e]cycloocten-6,11-imine;
1-chloro-6-methyl-5,6,11,12-tetrahydrodibenzo[a,e]cycloocten-6,11-imine;
10-chloro-6-methyl-5,6,11,12-tetrahydrodibenzo[a,e]cycloocten-6,11-imine;
6-ethyl-5,6,11,12-tetrahydrodibenzo[a,e]cycloocten6,11-imine;
8-bromo-6-methyl-5,6,11,12-tetrahydrodibenzo[a,e]cycloocten-6,11-imine;
11-hydroxy-6-methyl-5,6,11,12-tetrahydrodibenzo[a,e]cycloocten-6,11-imine;
6,13-dimethyl-5,6,11,12-tetrahydrodibenzo[a,e]cycloocten-6,11-imine;
and salts thereof.

Also included within the scope of the present invention are pharmaceutical compositions comprising the imines of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of an imine of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills or capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including polymeric acids and mixtures of polymeric acids with such materials as shellac, cetyl alcohol or cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil and peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone and gelatine.

The novel imines of this invention are useful as anticonvulsants at a dosage level of from about 0.01 to about 20 mg per kilogram of body weight, preferably about 0.05 to 2 mg/kg of body weight, on a regimen of 1 to 4 times a day.

In the treatment of neurodegeneration, a suitable dosage level is about 0.01 to 50 mg/kg/day, preferably about 0.05 to 10 mg/kg/day and especially about 0.05 to 1 mg/kg/day. The compounds may be administered on a regimen of 1 to 4 times per day.

The compounds of formula I above wherein $R^1$ is other than hydroxy may be prepared by a process which comprises reducing the compound of formula III:

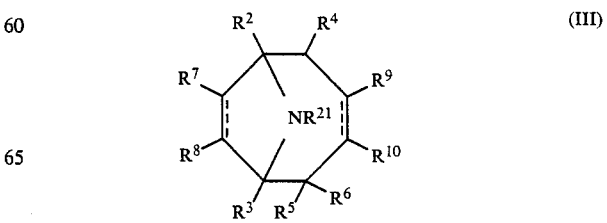

(III)

wherein $R^{21}$ represents hydroxy or $C_{1-6}$ alkoxy, and $R^2$ to $R^{10}$ are as defined with respect to formula I above; and, when $R^1$ is other than hydrogen, alkylation or alkenylation of the product. The preferred reducing agent is nascent hydrogen generated by the action of a metal, preferably zinc, with an acid, such as acetic acid. Suitable conditions for the process are a temperature of from 40° C. to 100° C. for 1 to about 10 hours.

The intermediate compounds of formula III may be prepared by reaction of a compound of formula IV:

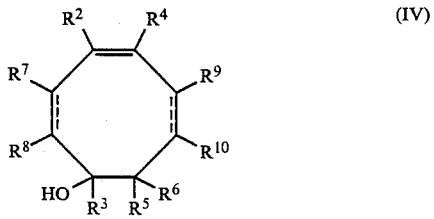

wherein $R^2$ to $R^{10}$ are as defined with reference to formula I above; with a hydroxylamine derivative $R^{21}NH_2$ in the presence of acid; followed by treatment with base such as sodium hydroxide.

In certain circumstances, the uncyclised intermediate compound of formula V will be isolated from the above process:

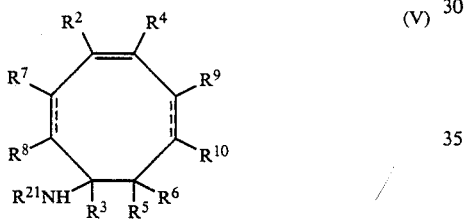

wherein $R^2$ to $R^{10}$ and $R^{21}$ are as hereinbefore defined. In order to effect complete conversion to the desired compound of formula III it will be necessary to treat the intermediate compound of formula V with a strong base, e.g. potassium t-butoxide.

Compounds of formula I above in which $R^2$ represents alkyl, carboxymethyl or halogen may be prepared by reacting a compound of formula VI:

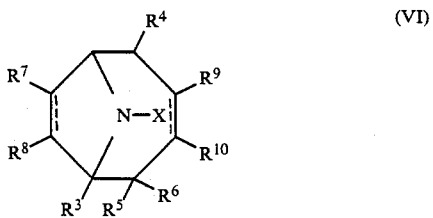

wherein $R^3$ to $R^{10}$ are as defined with respect to formula I above, and X represents a leaving group such as methoxy, p-toluenesulphonyloxy, p-toluenesulphonyl or halogen; with an anion $-R^2$.

The compounds of formula I in which the bridgehead groups $R^2$ and/or $R^3$ represent hydroxy may be prepared by methods analogous to those described in general terms in EP-A-No. 0264183. A further method is to treat the compound of formula III above, in which $R^2$ and/or $R^3$ is hydrogen, with manganese acetate, and subsequently to reduce the product thereby obtained with, for example, zinc in acetic acid.

This method may be illustrated by the following scheme:

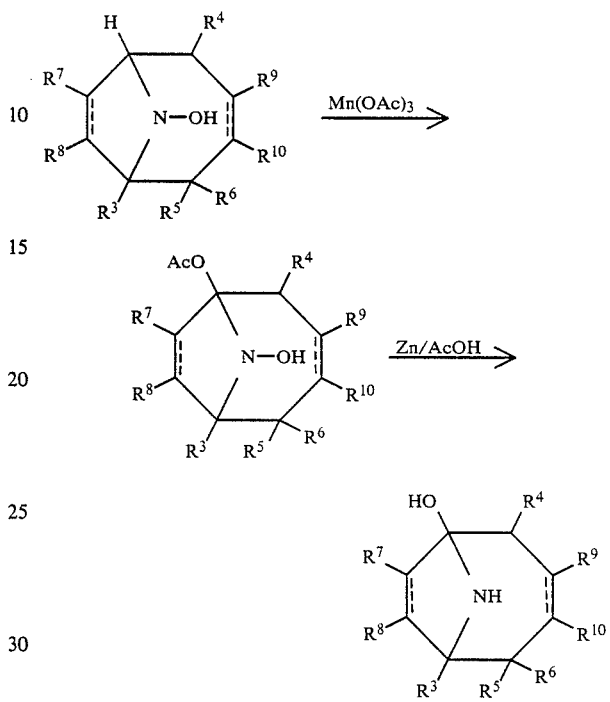

When it is desired that $R^1$ should be other than hydrogen, the resulting product can subsequently be alkylated or alkenylated.

The compounds of formula I in which $R^4$ and/or $R^5$ represent hydroxy when $R^6$ represents hydrogen may be prepared by reducing the corresponding oxo or dioxo compound, in which the nitrogen atom may be protected. The reduction may be effected by treatment with, for example, diisobutylaluminium hydride (Dibal-H) in an ethereal solvent such as ether, tetrahydrofuran or 1,2-dimethoxyethane at about $-90°$ to $-60°$ C., preferably about $-78°$ C., for about 1 to 3 hours.

This process produces a mixture of endo and exo hydroxy derivatives which, after deprotection, may be separated by conventional techniques such as preparative chromatography. Alternatively, in order to obtain the hydroxy compound selectively as its desired exo or endo isomer, the relevant oxo compound may be reduced with a chiral reducing agent such as D- or L-Selectride. Thus, it will be appreciated that a mixture of the exo and endo hydroxy isomers can be converted into a single desired exo or endo isomer by oxidation to the corresponding oxo compound and subsequent application of the foregoing selective reduction technique. This approach can equally be adopted for the conversion of a single exo or endo hydroxy isomer into the opposite isomer.

Further illustrative methods of preparing the exo and endo hydroxy compounds selectively in a related series are described in EP-A-No. 0264183.

The compounds of formula I wherein $R^2$, $R^3$ $R^4$ and/or $R^5$ represent fluoro may be prepared by treating the corresponding hydroxy compound with diethylaminosulphur trifluoride (DAST) in an inert organic solvent such as a chlorinated hydrocarbon, e.g.

chloroform or methylene dichloride, at about 15 to 30° C. for about 30 minutes to 2 hours.

In a further process of this invention, compounds having a fused saturated ring of formula VII:

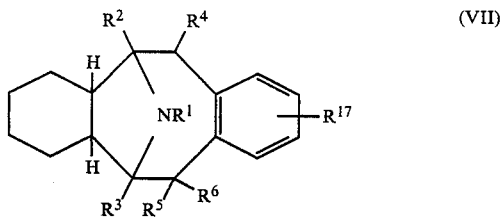

(VII)

wherein $R^1$ to $R^6$ and $R^{17}$ are as hereinbefore defined; may be prepared by reducing the corresponding dibenzo compound. A preferred reducing agent is hydrogen with a platinum catalyst. Alternatively the dibenzo compound can be treated with rhodium chloride ($RhCl_3.3H_2O$) in an ethanolic solution at about 15° to 40° C. for about 1 to 4 hours, followed by treatment with sodium borohydride ($NaBH_4$) at about 15° to 40° C. for about 1 to 5 hours.

Compound VII can also be prepared by hydrogenating the dibenzo starting material in ethanol in the presence of a rhodium on aluminium oxide ($Rh/Al_2O_3$) catalyst at about 40° to 70° C. starting at a pressure of about 500 to 1500 p.s.i. ($3.5 \times 10^5$ to $10.5 \times 10^5$ kgm$^{-2}$), for about 10 to 24 hours or until hydrogen is no longer consumed, followed by removal of catalyst and chromatographic separation of the components of the reduction product.

An additional process comprises hydrogenation of a dibenzo starting material or an N-hydroxy derivative thereof with 5 % palladium-on-carbon at about 50° to 100° C. and about 40 p.s.i (195 kgm$^{-2}$).

During any of the above reactions it may be necessary to protect any reactive groups on any of the molecules concerned with conventional protecting groups which may subsequently be removed using methods known from the art.

The compounds useful in this invention bind with a high affinity and in a reversible and saturable manner to membranes from rat brain cortex. In addition these compounds potently and selectively block responses to NMDA in a brain slice from rat cortex, and antagonise NMDA-induced seizures in the mouse.

Binding Studies

The compounds of the invention were tested for their ability to displace a standard compound from rat brain. The standard compound employed is 5-methyl-10,11-dihydro-5 H-dibenzo[a,d]cyclohepten5,10-imine, hereinafter referred to as MK-801.

Binding of [3 H]-MK-801 to rat brain in vitro was conducted in a crude synaptosomal membrane fraction (P2) prepared from rat cerebral cortex according to a modified method of Hulme et al., *Molecular Pharmacology*, 1978, 14, 737-750. Compounds of the invention displaced the [$^3$H]-MK-801 binding in a concentration-dependent manner. The concentrations of the compounds of accompanying Examples 1 to 19 required to displace 50% of specific [$^3$H]-MK-801 binding (IC$_{50}$) were below 5 μM in each case.

Cortical Slice Studies

The effects of compounds of the invention on responses to NMDA were assessed using the rat cortical slice as described by Wong et al., *Proc. Natl. Acad. Sci. USA*, 1986, 83, 7104. The apparent equilibrium constant ($K_b$) was calculated from the righthand shift in the NMDA concentration-response curve produced by the compound under test. The compounds of accompanying Examples 1 to 8, 12, 13 and 15 to 17 were tested and their $K_b$ values were found to be below 2 μM in each case.

Antagonism of NMDLA-induced seizures

Compounds of the invention were examined for their ability to antagonise tonic seizures induced by N-methyl-DL-aspartic acid (NMDLA). Groups of 8 male Swiss-Webster mice (25 to 30 g) were injected intravenously with the test compound at various doses, 15 min before s.c. administration of NMDLA (500 mg/kg). Animals were observed for the following 30 min and the number of mice protected from tonic extension of the forelimbs noted. ED$_{50}$ values for the antagonism of the NMDLA induced tonic seizures were determined using probit analysis. The compounds of accompanying Examples 1, 3, 15 and 16 were tested and their ED50 values were found to be below 5 mg/kg in each case.

The following Examples illustrate the preparation of compounds of this invention:

EXAMPLE 1

6-Methyl-5,6,11,12-tetrahydrodibenzo[a,e]cycloocten -6,11-imine Hydrochloride

Step A  5-Methylene-dibenzo[a,d]cycloheptene

To a solution of dibenzosuberenone (20.6g) in diethyl ether (200ml) at 0° C. under nitrogen, was added slowly with stirring, a solution of methyl lithium (100 ml of a 1.4M solution in diethyl ether). The solution was kePt at 0° C. for 10 minutes. then water (50 ml) added cautiously. The aqueous layer was discarded and the ether solution further washed with water (50 ml), dried and evaPorated to give crude methyl carbinol (20.2 g). This was dissolved in dichloromethane (100 ml), dichloroacetic acid (2 ml) was added and the red solution refluxed for 3 hrs. The solution was allowed to cool, washed with saturated aqueous sodium bicarbonate solution (50 ml), and water (25 ml), then dried and evaporated. The crude hydrocarbon was crystallised from n-hexane (17.2 g), mp 117°-9° C.

Step B  5-Hydroxymethyl-dibenzo[a,d]cycloheptene

To a solution of 5-methylene-dibenzo[a,d]cycloheptene (15q) in dry tetrahydrofuran (50 ml) at room temperature under nitrogen was added a solution of 9-BBN (160 ml of a 0.5M solution in tetrahydrofuran), and the solution refluxed under nitrogen for 3 h. The solution was cooled in ice, and 2N aqueous sodium hydroxide (250 ml) and 30% aqueous hydrogen peroxide (50 ml) were added. The cooled (ice-bath) mixture was stirred vigorously for 30 minutes then allowed to warm to room temperature. The mixture was extracted with ether (2×200 ml), the organic layer washed with water and brine. then dried and evaporated. Chromatography on silica gel eluting with 30% ethyl acetate in n-hexane gave pure alcohol (12.2 g), mp 86°-7° C.

Step C  5-p-Toluenesulphonyloxymethyl-dibenzo[a,d]cycloheptene

To a solution of 5-hydroxymethyl-dibenzo[a,d]cycloheptene (11.1 g) in dichloromethane (100 ml) was added p-toluenesulphonylchloride (9.5 g) and Pyridine (7.9 g. dried over KOH), and the solution stirred with drying tube Protection. A slight exothermic reaction was evident. After 2 h the reaction mixture was washed with water (50 ml) and the organic layer dried and evaporated. The residue was triturated with warm hexane and the solid Product collected and washed with hexane, then dried in vacuo to give the required tosylate (17.1 g), mp 139°–40° C.

Step D  5-Hydroxy-dibenzo[a,e]cyclooctene

To a solution of 5-p-toluenesulphonyloxymethyl-dibenzo[a,d]cycloheptene (17 g) in glacial acetic acid (150 ml) was added anhydrous sodium acetate (8.2 g) and the solution refluxed with stirring for 4 h. The solvents were removed in vacuo, the residue dissolved in methanol (100 ml), cooled to 0° C. and enough solid potassium hydroxide added to give pH 14. The suspension was stirred at room temperature for 2 h. then the methanol was removed in vacuo and the residue Partitioned between ether (200 ml) and water (50 ml). The organic layer was washed three times with water (50 ml), then dried and evaporated to qive the crude alcohol which was crystallised from n-hexane/5% ethyl acetate (10.2 g), mp 120°–1° C.

Step E  5-Oxo-dibenzo[a,e]cyclooctene

To a solution of oxalyl chloride (5 ml) in dry dichloromethane (75 ml) at −78° C. under nitrogen was added, dropwise. dimethyl sulphoxide (8.75 ml), and the solution stirred at −78° C. for 15 minutes. A solution of 5-hydroxy-dibenzo[a,e]cyclooctene (11.1 g) in dichloromethane (75 ml) was added over 5 minutes at −78° C. and the solution stirred for 15 minutes, then triethylamine (30 ml) was added and the mixture allowed to warm to room temperature. The mixture was washed with water (100 ml), 1N hydrochloric acid (50 ml) water (100 ml), brine (50 ml) then dried and evaporated to give the crude ketone which was recrystallised from ethyl alcohol/hexane (10.0 g), mp 112°–6 ° C.

Step F  5-Hydroxy-5-methyl-dibenzo[a,e]cyclooctene

To a stirred solution of 5-oxo-dibenzo[a,e]cyclooctene (10.0 g) in dry diethyl ether at 0° C. under nitrogen, was added over 5 minutes, through a canula, a solution of methyl lithium (40 ml of a 1.4M solution in diethyl ether). After a further 10 minutes stirring water (40 ml) was added cautiously and the separated aqueous layer discarded. The organic layer was washed with water. then dried and evaporated. Crystallisation from diethyl ether/hexane gave the pure alcohol (6.2 g), mp 108°–109° C.

Step G  13-Hydroxy-5-methyl-5,6,11,12 tetrahydrodibenzo[a,e]cycloocten-6,11-imine To a suspension of hydroxylamine hydrochloride (2.64 g) and anhydrous sodium acetate (3.11 g) in dichloromethane (25 ml) was added 5-hydroxy-5-methyl-dibenzo[a,e]cyclooctene (0.90 g). The mixture was stirred vigorously and brought to reflux under nitrogen. To the vigorously stirred refluxing suspension was added, over 10 minutes, dichloroacetic acid (8 ml) in dichloromethane (50 ml). The mixture was refluxed for 2 h, then allowed to cool to room temperature and 2N sodium hydroxide (60 ml) added. The organic layer was washed with water and brine, then dried and evaporated. Crystallisation from ethyl acetate/hexane gave the desired imine (370 mg), mp 159°–63° C.

Step H  6-Methyl-5,6,11,12-tetrahydrodibenzo[a,e]cycloocten-6,11-imine

To a solution of the hydroxy imine (Step G, 200 mg) in glacial acetic acid (3 ml) was added zinc powder (500 mg) and the suspension stirred at 68° C. overnight. The mixture was filtered, the cake washed with acetic acid (1 ml), then the filtrate was evaporated and partitioned between ether (10 ml) and 2N aqueous sodium hydroxide (10 ml). The ether layer was washed with water and brine. then dried and evaporated to give the crude Product as a buff solid. This was recrystallised from warm n-hexane to give 6-methyl-5,6,11,12-tetrahydrodibenzo[a,e]cycloocten-6,11-imine (110 mg). mp 125°–6°. The structure was confirmed by single crystal X-ray diffraction.

Step I  6-Methyl-5,6,11,12-tetrahydrodibenzo[a,e]cycloocten-6,11-imine hydrochloride To a solution of the imine (Step H. 50 mg) in ethyl acetate (2 ml) at room temperature was added a solution of saturated hydrogen chloride in ethyl acetate (2 ml). After 2 minutes a white Precipitate was deposited. This was collected by filtration. washed successively with ethyl acetate and dry ether and dried in vacuo to give pure 6-methyl-5,6,11,12tetrahydrodibenzo[a,e]cycloocten-6.11-imine hydrochloride (38 mg, mp 270°–275° C.), δ (CDCl$_3$, 360MH$_z$) 2.03 (3H, s, CH$_3$), 2.92 (1H, d, J=16.6 Hz, C(CH$_3$)—CH$_A$H$_B$), 3.17 (1H, d, J=16.8 Hz, and 5.7 Hz, CH$_C$H$_D$—CH$_E$(NH)), 4.10 (1H, d, J=16.8 Hz, CH$_C$H$_D$—CH$_E$(NH)), 4.24 (1H, d, J=16.6 Hz C(CH$_3$)—CH$_A$H$_B$), 5.13 (1H, m, CH$_C$H$_D$—CH$_E$(NH)), 6.79–7.18 (8H, m, ArH).

EXAMPLE 2

9-Bromo-6-methyl-5,6,11,12-tetrahydrodibenzo[a,e]cycloocten-6,11-imine hydrochloride Step A  2-Bromo-5-methylene-dibenzo[a,d]cycloheptene A solution of 2-Bromo-5-methylene-dibenzo[a,d]cyclohepten-5 -one (7.7 g) in anhydrous tetrahydrofuran (200 ml) was cooled to 0° C. and methyllithium (19.5 ml of a 1.4 molar solution) was added by syringe. After 15 minutes. water (50 ml) was added dropwise and the reaction mixture extracted with diethyl ether (3×100 ml). The combined organic phases were dried over sodium sulphate. filtered and concentrated in vacuo to give a colourless oil (6.5 g). δ (360 MH$_z$, CDCl$_3$) 1.6 (3H, br, s, CH$_3$), 6.9 (1H, d, J=12 Hz CH$_A$=CH$_B$), 7.0 (1H, d, J=12 Hz, CH$_A$=CH$_B$), 7.4–8.0 (7H, m, ArH). m/e 302 and 300 (M+). This was dissolved in dichloromethane (50 ml) with dichloroacetic acid (2.5 ml) and refluxed for 9 h. The solvent was removed in vacuo and the residue chromatographed on SiO$_2$ with 5% ethyl acetate in hexane as eluent to give the title compound as a colourless solid (5.8 g. mp 112°–114° C.). δ (360 MHz, CDCl$_3$) 5.24 (1H, d. J=1.4 Hz, =CH$_A$H$_B$), 5.26 (1H, d, J=1.4 Hz=CH$_A$H$_B$), 6.71 (1H, d, J=12 Hz, CH$_C$=CH$_D$), 6.85 (1H, d, J=12 Hz, CH$_C$=CH$_D$), 7.2–7.5 (7H, m, ArH). m/e 284 and 282 (M+).

Step B
2-Bromo-5-hydroxymethyl-dibenzo[a,d]cycloheptene

To a solution of 2-bromo-5-methylene-dibenzo[a,d]cycloheptene (5.7 g) in dry THF (20 ml), under an inert atmosphere, was added 9-borabicyclo[3,3,1]nonane (4.4 ml of a 0.5 molar solution in THF) at ambient temperature, and the reaction mixture was then refluxed for 3 h. After cooling in an ice bath the reaction was quenched by the slow addition of 2N sodium hydroxide solution (100 ml) and 30% hydrogen peroxide (20 ml). After stirring vigorously at 0° C. for 45 minutes the reaction mixture was allowed to warm to room temperature over a 2 h period then extracted with diethyl ether (3×200 ml). The combined organic layers were washed with brine (1×100 ml), dried ($Na_2SO_4$), filtered and concentrated in vacuo to leave a residue which was purified by chromatography on flash silica with 30% ethyl acetate in hexane as eluent to give the title compound (6.0 g) as a colourless oil. δ (360 MHz, $CDCl_3$) 3.81 (2H, d, J=7.9 Hz, CH—$CH_2$OH), 4.17 (1H, t, J=7.9 Hz, C$\underline{H}$—$CH_2$OH), 6.75 (1H, d, J=12 Hz, C$\underline{H}_A$=$CH_B$), 6.89 (1H, d, J=12 Hz, $CH_A$=C$\underline{H}_B$), 7.15-7.48 (7H, m, ArH).

Step C
2-Bromo-5-p-toluenesulphonyloxymethyl-dibenzo [a,d]cycloheptene

To a solution of 2-bromo-5-hydroxymethyl-dibenzo [a,d]cycloheptene (6.1 g) in dry dichloromethane (60 ml) was added p-toluenesulphonyl chloride (4.9 g). pyridine (4 g) and 4-dimethylamino pyridine (100 mg). The reaction mixture was refluxed for 14 h, cooled, washed with water (2×50 ml), dried ($Na_2SO_4$), filtered and concentrated in vacuo. The residue. was purified by flash silica chromatography using 10% ethyl acetate in hexane as eluent to give the title compound as a colourless oil (8.2 g). δ (360 MHz, $CDCl_3$) 2.46 (3H, s, $CH_3$), 4.12 (1H, dd J=6.2 and 3.5 Hz, C$\underline{H}$—$CH_2$—O), 4.24-4.32 (2H, m, CH—$CH_2$—O), 6.50 (1H, d, J=11.9 Hz, C$\underline{H}_A$=$CH_B$), 6.73 (1H, d, J=11.9 Hz, $CH_A$=C$\underline{H}_B$), 7.10-7.40 (11H, m, ArH).

Step D  2-Bromo-5-hydroxy-dibenzo[a,e]cyclooctene and 2-bromo-6-hydroxy dibenzo[a,e]cyclooctene To a solution of 2-bromo-5-p-toluenesulphonyloxymethyl-dibenzo[a,d]cycloheptene (8.1 g) in glacial acetic acid (75 ml) was added anhydrous sodium acetate (2.9 g). The reaction mixture was refluxed for 24 h then the solvent removed under vacuum to leave a residue which was partitioned between dichloromethane (3×100 ml) and water (100 ml). The combined organic layers were dried ($Na_2SO_4$), filtered and concentrated in vacuo to leave a residue which was dissolved in 75% aqueous methanol (100 ml) and treated with potassium hydroxide (4 g). After 14 h the reaction mixture was concentrated in vacuo and the residue partitioned between water (50 ml) and diethyl ether (3×50 ml). The combined organic layers were dried ($Na_2SO_4$), filtered and concentrated in vacuo. Chromatography of the residue on flash silica with 10% ethyl acetate in hexane as eluent gave the less polar isomer, 2-bromo-5-hydroxy-dibenzo[a,e]cyclooctene (2.54 g, m.p. 148°-151° C.). δ (360 MHz, $CDCl_3$) 3.26 (1H, dd, J=13.9 and 9.9 Hz, C$\underline{H}_A H_B$—CHOH), 3.46 (1H, dd, J=13.9 and 6.2 Hz, C$\overline{H}_A \underline{H}_B$—CHOH), 5.24 (1H, dd, J=9.9 and 6.2 Hz, C$\underline{H}$OH), 6.76 (1H, d, J=12.1 Hz, C$\underline{H}_C$=$CH_D$), 6.87 (1H, d, J=12.1 Hz, $CH_C$=C$\underline{H}_D$), 7.09-7.35 (7H, m, ArH), m/e 302 and 300 (M+); and as an oil the more polar isomer 2-bromo-6-hydroxy-dibenzo[a,e]cyclooctene (1.04 g), 67 (360 MHz, $CDCl_3$) 3.25 (1H, dd, J=13.8 and 10.0 Hz C$\underline{H}_A H_B$—CHOH), 3.40 (1H, dd, J=13.8 and 6.4 Hz, C$\overline{H}_A \underline{H}_B$—CHOH), 5.26 (1H, dd, J=10.0 and 6.4 Hz, C$\overline{H}_A \underline{H}_B$—CHOH), 6.75 (1H, d, J=12.1 Hz, C$\underline{H}_C$=$CH_D$), 6.90 (1H, d, J=12.1 Hz, $CH_C$=C$\underline{H}_D$), 7.08-7.45 (7H, m, ArH). m/e 302 and 300 (M+).

Step E  2-Bromo-5-oxo-dibenzo[a,e]cyclooctene

To a solution of 2-bromo-5-hydroxy-dibenzo[a,e]cyclooctene (2.3 g) in dry dichloromethane (100 ml) was added pyridinium dichromate (5.75 g) and crushed 4 A molecular sieves (3 g). After stirring at room temperature for 14 h, diethyl ether (200 ml) was added and the reaction mixture was filtered through a plug of celite. The solvent was removed in vacuo and the residue purified by chromatography on flash silica with 5% ethyl acetate in hexane as eluent to give as a colourless solid. the title compound (2.1 g, m.p. 121°-123° C.). δ (360 MHz, $CDCl_3$) 4.03 (2H, s, $CH_2$), 6.92 (1H, d, J=12.8 Hz, C$\underline{H}_A$=$CH_B$), 7.09 (1H, d, J=12.8 Hz, $CH_a$=C$\underline{H}_B$), 7.20-7.56 (6H, m, ArH), 8.08 (1H, d, J=8.5 Hz, BrC=CH—C$\underline{H}$=C—C=O). m/e 300 and 298 (M+).

Step F
9-Bromo-13-hydroxy-6-methyl-5,6,11.12tetrahydrodibenzo[a,e]cyclooctcen-6,11-imine To a solution of 2-bromo-5-oxo-dibenzo[a,e]cyclooctene (1 g) in dry diethyl ether (20 ml) at 0° C. under an atmosphere of nitroqen was added methyl lithium (2.2 ml of a 1.6 molar solution). After 3 h at room temperature the reaction mixture was cooled to 0° C. quenched dropwise with water (20 ml) and extracted with diethyl ether (3×30 ml). The combined orqanic layers were dried ($Na_2SO_4$), filtered and evaporated in vacuo to leave an oil (1.03 g), which was dissolved in dry dichloromethane (15 ml) and added to a solution containing dichloroacetic acid (4.1 ml), sodium acetate (2.7 g) and hydroxylamine hydrochloride (2.3 g) in dichloromethane (55 ml) which had been prepared 2 hours previously. The reaction mixture was stirred at room temperature for 6 h then refluxed for a further 6 h. After cooling, 2N potassium hydroxide solution was added until the pH was 14 and the twophase mixture was vigorously stirred for 30 minutes. The organic layer was separated. washed with water (1×50 ml) and brine (1×50 ml), dried ($Na_2SO_4$), filtered and concentrated in vacuo. The crude residue was triturated with hot hexane to produce the required product as a white crystalline solid which was collected by filtration (0.17 g, m.p. 147°-149° C.). The spectrum (360 MHz, $CDCl_3$) showed a complex mixture containing two atropisomers.

Step G
9-Bromo-6-methyl-5,6,11,12-tetrahydrodibenzo a,e]cyloocten-6,11-imine hydrochloride To a solution of 9-bromo-13-hydroxy-6-methyl5,6,11,12-tetrahydrodibenzo[a,e]cycloocten-6,11-imine (0.1 g) in glacial acetic acid (4 ml) was added zinc dust (0.2 g). The reaction mixture was heated at 70° C. under an inert atmosphere for 6 h then filtered and concentrated in vacuo to leave a residue which was partitioned between dichloromethane (30 ml) and dilute sodium hydroxide solution (30 ml). The organic layer was separated, dried (Na$_2$SO$_4$), filtered and evaporated to leave a residue which was dissolved in 5 molar hydrogen chloride in ethyl acetate (15 ml). The solvent was evaporated to leave a solid which was recrystallised frox ethyl acetate/diethylether. The title compound (0.07 g, m.p. 172°–175° C.) was collected by filtration and dried under high vacuum. δ (DMSO, 360 MHz) 1.87 (3H, s, CH$_3$), 3.11 (1H, d, J=16.4 Hz, PhCH$_A$H$_B$—C(NH)CH$_3$), 3.25 (1H, dd, J=16.7 and 5.0 Hz, PhCH$_C$H$_D$—C(NH)H$_E$), 3.69 (1H, d, J=16.7 Hz, PhCH$_C$H$_D$—C(NH)H$_E$), 3.84 (1H, d, J=16.4 Hz, PhCH$_A$H$_B$—C(NH)CH$_3$), 5.16 (1H, d, J=5.0 Hz, PhCH$_C$H$_d$—C(NH)H$_E$), 6.88–6.98 (4H, m, ArH), 7.19 (1H, d, J=8.1 Hz, CH$_F$=CH$_G$—CBr=CH$_H$), 7.37 (1H. dd, J=8.1 and 1.8 Hz, CH$_F$=CH$_G$—CBr—CH$_H$, 7.51 (1H, d, J=1.8 Hz, CH$_F$=CH$_G$—CBr=CH$_H$). n.O.e.'s observed from CH$_3$ to H$_F$ and H$_H$ to H$_E$.

EXAMPLE 3

2-Bromo-6-methyl-5,6,11,12-tetrahydrodibenzo[a,e]cycloocten-6.11-imine hydrochloride Step A  2-Bromo-6-oxo-dibenzo[a,e]cyclooctene To a solution of 2-bromo-6-hydroxy-dibenzo[a,e]cyclooctene (1.0 g) in dry dichloromethane (50 ml) was added pyridinium dichromate (2.75 g) and crushed 4 A molecular sieves (1.5 g). After stirring at room temperature for 14 h, diethyl ether (150 ml) was added and the reaction mixture was filtered through a plug of celite. The solvent was removed in vacuo and the residue purified by chromatography on flash silica with 5% ethyl acetate in hexane as eluent to give. as a colourless solid. the title compound (0.76 g, m.p. 147°–150° C.). δ (360 MHz. CDCl$_3$) 4.01 (2H, s, CH$_2$—C=O), 6.96 (1H, d, J=12.7 Hz, CH$_A$=CH$_B$), 7.06 (1H, d, J=12.7 Hz, CH$_A$=CH$_B$), 7.25–7.52 (6H. m, ArH), 8.21 (1H, d, J=8.0 Hz, C(O)C=CH—CH=CH—CH). m/e 302 and 300 (M+).

Step B
2-Bromo-13-hydroxy-6-methyl-5,6,11,12tetrahydrodibenzo[a,e]cycloocten-6,11-imine To a solution of 2-bromo-6-oxo-dibenzo[a,e]cyclooctene (0.7 g) in dry diethyl ether (30 ml) at 0° C. under atmosphere of nitrogen was added methyl magnesium bromide (2 ml of a 3 molar solution). After 4 h at room temperature the reaction mixture was cooled to 0° C. quenched by the dropwise addition of saturated ammonium sulphate solution (20 ml) and extracted into diethyl ether (3×30 ml). The combined organic layers were dried (Na$_2$SO$_4$) filtered and evaporated to leave an oil (0.72 g) which was dissolved in dry dichloromethane (10 ml) and added to a solution containing dichloroacetic acid (3.1 ml). sodium acetate (2.1 g) and hydroxylamine hydrochloride (1.7 g) in dichloromethane (40 ml) which had been prepared 2 hours previously. The reaction mixture was stirred at room temperature for 6 h then refluxed for a further 6 h. After cooling, 2N potassium hydroxide solution was added until the pH was 14 and the two phase mixture was stirred vigorously for 30 minutes. The organic layer was separated. washed with water (1×40 ml) and brine (1×40 ml), dried (Na$_2$SO$_4$), filtered and concentrated in vacuo. The crude residue was purified by chromatography on flash silica with 30% ethyl acetate in hexane to give, as a colourless foam, the title compound (0.15 g). The nmr spectrum (360 MHz, CDCl$_3$) showed a mixture of two atropisomers. m/e 331 and 329 (M+).

Step C
2-Bromo-6-methyl-5,6,11,12-tetrahydrodibenzo[a,e]-cycloocten-6,11 imine hydrochloride To a solution of 2-bromo-13-hydroxy-6-methyl-5,6, 11,12-tetrahydroditenzo[a,e]cycloocten-6 ,11-imine (0.14 g) in glacial acetic acid (5 ml) was added zinc dust (0.28 g). The reaction mixture was heated at 65° C. under an atmosphere of nitrogen for 6 h then filtered and concentrated in vacuo to leave a residue which was partitioned between dichloromethane (30 ml) and dilute sodium hydroxide solution (30 ml). The organic layer was separated. dried (Na$_2$SO$_4$) filtered and evaporated to leave a res which was dissolved in 5 molar hyrogen chloride in ethyl acetate (20 ml). The solvent was evaporated to leave a solid which was recrystallised from ethyl acetate/ diethyl ether. The title compound (0.04 g, m.p. 189°–191° C.) was collected by filtration and dried under high vacuum. δ (DMSO, 360 MHz) 1.88 (3H, s, CH$_3$), 3.12 (1H, d, J=16.7 Hz, C(CH$_3$)CH$_A$H$_B$), 3.36 (1H,dd, J=16.7 and 5.9 Hz CH$_C$H$_D$CH$_F$(NH)), 3.72 (1H, d, J=16.7 Hz, CH$_C$H$_D$CH$_E$(NH), 3.83 (1H, d, J=16.5 Hz, C(CH$_3$)—CH$_A$H$_B$), 5.19 (1H, d, J=5.9 Hz, CH$_C$H$_D$CH$_E$(NH), 6.84 (1H. d, J=8.1. Hz, CH$_F$=CH$_G$—CBr=CH), 7.12 (1H. dd, J=8.1 and 2.0 Hz, CH$_F$=CH$_G$—CBr=CH), 7.17–7.42 (5H. m, ArH). n.O.e.'s observed from CH$_3$ and from H$_E$ to the aromatic protons on the unsubstituted ring; and trom H$_F$ to H$_A$ and H$_F$ to H$_G$.

EXAMPLE 4

9-Chloro-6-methyl-5,6,11,12-tetrahydrodibenzo[a,e]cycloocten-6.11-imine hydrochloride Step A  2-Chloro-5-methylene-dibenzo a,d]cycloheptene A solution of 2-chloro-dibenzo[a d]cyclohepten-5 -one (8.7 g) in anhydrous diethyl ether (200 ml) was cooled to 0° C. and methyllithium (38 ml of a 1.4 molar solution) was added by syringe. After 20 minutes, water (50 ml) was added dropwise and the reaction mixture extracted with diethyl ether (3×100 ml). The combined organic layers Were dried over sodium sulphate, filtered and concentrated in vacuo to give a colourless oil (9.3 g). This was dissolved in dichloromethane (200 ml) with dichloroacetic acid (3 ml) and refluxed for 1H. The mixture was cooled, washed with saturated sodium hydrogen carbonate solution (1×100 ml) and brine (1×100 ml), dried (Na$_2$SO$_4$), filtered and concentrated in vacuo to give the title compound as a colourless solid (8.4 g, m.p. 100°–102° C.) δ (360 MHz, CDCl$_3$) 5.24 (1H, d, J =1.4 Hz, , 5.26 (1H, d, J=1.4 Hz, CH$_A$H$_B$), 6.72 (1H, d, J=12 Hz, CH$_C$=CH$_D$), 6.86 (1H, d, J=12 Hz, CH$_C$=CH$_D$), 7.24–7.39 (7H, m, ArH). m/e 240 and 238 (M+).

Step D  8
2-Chloro-5-hydroxymethyl-dibenzo[a,d]cycloheptene

To a solution of 2-chloro-5-methylene-dibenzo[a,d]cycloheptene (8.3 g) in dry tetrahydrofuran (30 ml). under an inert atmosphere, was added 9-borabicyclo [3.3.1]nonane (71 ml of a 0.5 molar solution in tetrahydrofuran) at ambient temperature and the reaction mixture was then refluxed for 3 h. After cooling. the reaction was quenched by the slow addition of 2N sodium hydroxide solution (180 ml) and 30% hydrogen peroxide (36 ml). After stirring vigorously at 0° C. for 45 minutes the reaction mixture was allowed to warm to room temperature over a 2 h period then extracted into diethyl ether (3×250 ml). The combined organic layers were washed with brine (1×150 ml), dried (Na$_2$SO$_4$), filtered and concentrated in vacuo to leave a residue which was purified by chromatography on flash silica with 40% ethyl acetate in hexane as eluent to give the title compound (8.1 g) as a colourless oil. δ (360 MHz, CDCl$_3$) 3.80 (2H. d, J=7.9 Hz CH—CH$_2$OH), 4.18 (1H, t, J=7.9 Hz, CH—CH$_2$OH), 6.76 (1$\overline{\text{H}}$, d, J=11.9 Hz, CH$_A$=CH$_B$) 6.89 (1H, d, J=11.9 Hz, CH$_A$=CH$_B$), 7.24–7.38 (7H, m, ArH); m/e 258 and 256 (M+)

Step C

2-Chloro-5-hydroxy-dibenzo[a,e]cyclooctene and 2-chloro-6-hydroxy-dibenzo[a,e]cyclooctene To a solution of 2-chloro-5-hydroxymethyl-dibenzo [a,d]cycloheptene (8.1 g) in dry dichloromethane (70 ml) was added p-toluene sulphonyl chloride (6.7 g). pyridine (2.9 ml) and 4-dimethylamino pyridine (100 mg). The reaction mixture was refluxed for 14 h, cooled. washed with water (2×50 ml), dried (Na$_2$SO$_4$) filtered and concentrated in vacuo to leave an oil which was purified by chromatography on flash silica with 10% ethyl acetate in hexane as eluent. The purified tosylate was dissolved in glacial acetic acid (70 ml) with anhydrous sodium acetate (7.4 g) and refluxed for 14 h. The mixture was concentrated in vacuo to leave a residue which was partitioned between dichloromethane (3×100 ml) and water (100 ml). The combined organic layers were dried (Na$_2$SO$_4$), filtered and concentrated in vacuo to leave a residue which was dissolved in 75% aqueous methanol (150 ml) and treated with potassium hydroxide (10 g). After 11 h the reaction mixture was concentrated in vacuo and the residue partitioned between water (75 ml) and diethyl ether (3×75 ml). The combined organic layers were dried (Na$_2$SO$_4$), filtered and concentrated in vacuo. Chromatography of the residue on flash silica with 15% ethyl acetate in hexane as eluent gave the less polar isomer 2-chloro-5-hydroxydibenzoa[a,e]cyclooctene (2.9 g, m.p. 148°–149° C.). δ (360 MHz, CDCl$_3$) 3.26 (1H, dd, J=14.0 and 9.9 Hz, CH$_A$H$_B$—CHOH), 3.46 (1H, dd, J=14.0 and 6.3 Hz, C$\overline{\text{H}}_A$H$_B$—CHOH), 5.27 (1H, dd, J=9.9 and 6.3 Hz, CH$_A$$\overline{\text{H}}_B$—CHOH, 6.77 (1H, d J=12.0 Hz, CH$_C$=CH$_D$), 6.87 (1H, d, J=12.0 Hz, CH$_C$=CH$_D$), 7.08–7.41 (7H, m, ArH). m/e 258 and 256 (M+); and as an oil, the more polar isomer 2-chloro-6-hydroxy-dibenzo[a,e]cyclooctene (1.7 g) δ (360 MHz CDCl$_3$) 3 ,27 (1H. dd, J=13.8 and 10.0 Hz, CH$_A$H$_B$—CHOH), 3.41 (1H. dd, J=13.8 and 6.3 Hz, C$\overline{\text{H}}_A$H$_B$—CHOH), 5.25 (1H, dd, J=10.0 and 6.3 Hz, CH$_A$$\overline{\text{H}}_B$—CHOH), 6.75 (1H, d, J=12.0 Hz. CH$_C$=CH$_D$), 6.90 (1$\overline{\text{H}}$, d, =12.0 Hz, CH$_C$=CH$_D$), 7.07–7.44 (7H, m, ArH). m/e 258 and 256 (M+).

Step D 2-Chloro-5-oxo-dibenzo[a,e]cyclooctene

To a solution of 2-chloro-5-hydroxy-dibenzo[a,e]cyclooctene (1.5 g) in dry dichloromethane (60 ml) was added pyridinium dichromate (5 g) and crushed 4 A molecular sieves (2.5 g). After stirring at room temperature for 14 h, diethyl ether (150 ml) was added and the reaction mixture was filtered through a plug of celite. The solvent was removed in vacuo and the residue purified by chromatography on flash silica with 5% ethyl acetate in hexane as eluent to give. as a colourless oil, the title compound (1.4 g). δ (360 MHz, CDCl$_3$) 4.04 (2H. s, CH$_2$), 6.93 (1H, d, J =12.9 Hz, CH$_A$=CH$_B$), 7.10 (1H. d, J=12.9 Hz, CH$_A$=CH$_B$), 7.22–7.42 (6H, m, ArH), 8.17 (1H. d, J =8.4 Hz, ClC=CH—C$\overline{\text{H}}$ =C—C=O). m/e 256 and 254 (M+).

Step E

9-Chloro-13-hydroxy-6-methyl-5,6,11,12-tetrahydrodibenzo[a,e]cycloocten-6,11-imine To a solution of 2-chloro-5-oxo-dibenzo[a,e]cyclooctene (1.4 g) in dry diethyl ether (50 ml) at 0° C. under an atmosphere of nitrogen was added methyllithium (4 ml of a 1.6 molar solution). After 3 h at room temperature the reaction mixture was cooled to 0° C. quenched dropwise with water (30 ml) and extracted with diethyl ether (3×30 ml). The combined organic layers were dried (Na$_2$SO$_4$), filtered and evaporated to leave an o 1.73 g). which was dissolved in dry dichloromethane (15 ml) and added to a solution containing dichloroacetic acid (12.2 ml) sodium acetate (5.2 g) and hydroxylamine hydrochloride (1.4 g) in dichloromethane (70 ml) which had been prepared 2 hours previously. The reaction mixture was stirred at room temperature for 2 h then refluxed for a further 3 h. After cooling. 2N potassium hydroxide solution was added until the pH was 14 and the two phase mixture was stirred vigorously for 30 minutes. The organic layer was separated, washed with water (1×60 ml) and brine (1×60 ml), dried (Na$_2$SO$_4$), filtered and concentrated in vacuo. The crude residue was triturated with hot hexane to Produce the title compound (0.2 g, m.p. 182° C.). The nmr spectrum (360 MHz, CDCl$_3$) showed a mixture of two atropisomers.

Step F  9-Chloro-6-methyl-5 6 11.12-tetrahydrodibenzo [a,e]cycloocten-6 11-imine hydrochloride To a solution of 9-chloro-13-hydroxy-6-methyl5,6,11,12-tetrahydrodibenzo[a,e]cycloocten-6,11-imine (0.1 g) in glacial acetic acid (3 ml) was added zinc dust (0.2 g). The reaction mixture was heated at 70° C. under an inert atmosphere for 11 h then filtered and concentrated in vacuo to leave a residue which was partitioned between dichloromethane (30 ml) and dilute sodium hydroxide solution (30 ml). The organic layer was separated, dried (Na$_2$SO$_4$), filtered and evaporated to leave an oil which was dissolved in 5 molar hydrogen chloride in ethyl acetate (15 ml). The solvent was evaporated to leave a solid which was recrystallised from ethyl acetate/diethyl ether. The title compound (0.064 g, m.p. 187°–191° C.) was collected by filtration and dried under high vacuum. δ (DMSO, 360 MHz) 1.89 (3H, s, CH$_3$), 3.09 (1H, d, J=16.5 Hz, PhCH$_A$—C(NH)CH$_3$), 3.27 (1H, dd, J=16.7 Hz and 4.91 Hz, PhCH$_C$—C(NH)CH$_3$), 3.73 (1H, d, J=16.7 Hz, CH$_C$H$_D$—C(NH)H$_E$), 3.89 (1H, d, J=16.5 Hz, CH$_A$H$_B$—C(NH)CH$_3$), 5.17 (1H, d, J=4.9 Hz, PhCH$_C$H$_D$—C(NH)H$_E$), 6.90–6.97 (4H, m, ArH), 7.23–7.27 (2H, m, ArH), 7.37 (1H, s, CH$_F$=CBr—CH=CH). n.o.e.'s observed from H$_E$ to H$_F$ and CH$_3$ to δ 7.25 (one of the two other protons on the chlorine substituted aromatic ring). m/e 271 and 269 (M+).

EXAMPLE 5

2-Chloro-6-methyl-5,6,11,12-tetrahydrodibenzo[a,e]cycloocten-6,11-imine hydrochloride

Step A   2-Chloro-6-oxo-dibenzo[a,e]cyclooctene

To a solution of 2-chloro-6-hydroxy-dibenzo[a,e]cyclooctene (1.6 g) in dry dichloromethane (80 ml) was added pyridinium dichromate (4.3 g) and crushed 4 A molecular sieves (2.5 g). After stirring at room temperature for 14 h. diethyl ether (200 ml) was added and the reaction mixture was filtered through a plug of celite. The solvent was removed in vacuo and the residue purified by chromatography on flash silica with 5% ethyl acetate in hexane as eluent to give, as a colourless oil. the title compound (0.7 g). δ (360 MHz, CDCl$_3$) 4.03 (2H, s, CH$_2$—C=O), 6.97 (1H, d, J=12.8 Hz, CH$_A$=CH$_B$), 7.06 (1H, d, J=12.8 Hz, CH$_A$=CH$_B$), 7.23–7.53 (6H, m, aromatics), 8.22 (1H, d, J=7.9 Hz, C(O)C=CH—CH=CH—CH). m/e 256 and 254 (M+).

Step B   2-Chloro-13-hydroxy-6-methyl-5,6,11,12-tetrahydrodibenzo[a e]cycloocten-6,11-imine To a solution of 2-bromo-6-oxo-dibenzo[a,e]cyclooctene (0.67 g) in dry diethyl ether (40 ml) at 0° C. under nitrogen was added methyl magnesium bromide (1.8 ml of a 3 molar solution). After 4 h at room temperature the reaction mixture was cooled to 0° C. quenched by the dropwise addition of saturated ammonium sulphate solution (15 ml) and extracted into diethyl ether (3×25 ml). The combined organic layers were dried (Na$_2$SO$_4$), filtered and evaporated to leave an oil which was dissolved in dry dichloromethane (10 ml) and added to a solution containing dichlorcacetic acid (3.2 ml), sodium acetate (2.1 g) and hydroxylamine hydrochloride (1.8 g) in dichloromethane (35 ml), which had been prepared 2 h previously. The reaction mixture was stirred at room temperature for 6 h then refluxed for a further 8 h. After cooling. 2N potassium hydroxide was added until the pH was 14 and the two phase mixture was stirred vigorously for 30 minutes. The organic layer was separated, washed With water (1×40 ml) and brine (1×40 ml), dried (Na$_2$SO$_4$), filtered and concentrated in vacuo. The crude residue was purified by chromatoqraphy on flash silica with 30% ethyl acetate in hexane to give, as a colourless foam, the title compound (0.08 g). The nmr spectrum (360 MHz, CDCl$_3$) showed a mixture of two atropisomers. m/e 287 and 285 (M+).

Step C   2-Chloro-6-methyl-5,6,11,12-tetrahydrodibenzo[a,e]-cycloocten-6,11-imine hydrochloride To a solution of 2-chloro-13-hydroxy-6-methyl-5,6,11,12-tetrahydrodibenzo[a,e]cycloocten-6,11-imine (0.065 g) in glacial acetic acid (5 ml) was added zinc dust (0.13 g). The reaction mixture was heared at 65° C. under an atmosphere of nitrogen for 8 h. then filtered and concentrated in vacuo to leave a residue which was partitioned between dichloromethane (30 ml) and dilute sodium hydroxide solution (30 ml). The organic layer was separated. dried (Na$_2$SO$_4$) filtered and concentrated in vacuo to leave a residue which was dissolved in 5 molar hydrogen chloride in ethyl ether (15 ml). The solvent was evaporated to leave a solid which was recrystallised from ethyl acetate/diethyl ether. The title compound (0.043 g, m.p. 174°–176° C.) was collected by filtration and dried under high vacuum. δ (DMSO, 360 MHz) 1.89 (3H, s, CH$_3$), 3.14 (1H, d, J=16.5 Hz, C(CH$_3$)CH$_A$H$_B$), 3.34 (1H, dd, J=16.8 and 6.1 Hz, CH$_C$H$_D$CH$_E$(NH)), 3.70 (1H, d, J=16.8 Hz, CH$_C$H$_D$CH$_E$(NH)), 3.84 (1H, d, J=16.5 Hz, C(CH$_3$)CH$_A$H$_B$), 5.20 (1H, d, J=6.1 Hz, CH$_C$H$_D$CH$_E$(NH)), 6.90 (1H, d, J=8.2 Hz, CH$_F$=CH$_G$—CCl=CH$_H$), 6.99 (1H, dd, J=8.1 and 2.1 Hz, CH$_F$=CH$_G$—CCl=CH$_H$), 7.04 (1H, d, J=2.1 Hz, CH$_F$=CH$_G$—CCl=CH$_H$), 7.17–7.27 (4H, m, ArH). n.O.e.'s observed from CH$_3$ and from H$_E$ to the aromatic protons on the unsubstituted ring.

EXAMPLE 6

8-Bromo-6-methyl-5,6,11,12-tetrahydrodibenzo[a,e]cycloocten-6,11-imine hydrochloride

Step A   3-Bromo-5-methylene-dibenzo[a,d]cycloheptene

To a solution of 3-bromo-dibenzo[a,d]cyclohepten5-one (4.1g) in anhydrous tetrahydrofuran (50 ml) at 0° C. under nitrogen was added methyllithium (10.7 ml of a 1.4 molar solution) by syringe. After 15 minutes. water (30 ml) was added dropwise and the reaction mixture extracted with diethyl ether (3×100 ml). The combined organic layers were dried (Na$_2$SO$_4$), filtered and concentrated in vacuo to give a colourless oil (4.2 g) which was dissolved in dichloromethane (30 ml) with dichloroacetic acid (1ml) and refluxed for 9 h. The solvent was removed under vacuum to leave a residue which was purified by chromatography on flash silica with 5% ethyl acetate in hexane as eluent to give. as a colourless oil. the title compound (3.9 g). δ (360 MHz, CDCl$_3$) 5.28 (2H, s, C=CH$_2$), 6.75 (1H, d, J=12 Hz, CH$_A$=CH$_B$), 6.84 (1H, d, J=12 Hz, CH$_A$=CH$_B$), 7.10–7.55 (7H, m, ArH). m/e 284 and 282 (M+).

Step B   3-Bromo-5-hydroxymethyl-dibenzo[a,d]cycloheptene

To a solution of 3-bromo-5-methylene-dibenzo[a,d]cycloheptene (3.8 g) in dry tetrahydrofuran (20 ml). under an inert atmosphere. was added 9-borabicyclo [3.3,1]nonane (30 ml of a 0.5 molar solution in tetrahydrofuran) at ambient temperature and the reaction mixture was refluxed for 3 h. After cooling in an ice bath the reaction was quenched by the slow addition of 2N sodium hydroxide solution (100 ml) and 30% hydrogen peroxide (20 ml). After stirring vigorously at 0° C. for 45 minutes the reaction mixture was allowed to warm to room temperature over a 2 hour period then extracted with diethyl ether (3×200 ml). The combined organic layers were washed with brine (1×100 ml), dried (Na$_2$SO$_4$) filtered and concentrated in vacuo to leave a residue which was purified by chromatography on flash silica with 30% ethyl acetate in hexane as eluent to give the title compound (2.3 g) as a colourless oil. δ (CDCl$_3$, 360 MHz) 3.83 (2H, d, J=7.9 Hz, CH$_2$OH), 4.13 (1H, t, J=7.9 Hz, CH—CH$_2$OH), 6.78 (1H, d, J=12 Hz, CH$_A$=CH$_B$), 6.87 (1H, d, J=12 Hz, CH$_A$=CH$_B$), 7.17–7.50 (7H, m, ArH). m/e 302 and 300 (M+).

Step C   3-Bromo-5-hydroxy-dibenzo[a,e]cyclooctene and 3-bromo-6-hydroxy-dibenzo[a,e]cyclooctene To a solution of 3-bromo-5-hydroxymethyldibenzo[a,d]cycloheptene (2.2 g) in dry dichloromethane (50 ml) was added p-toluene sulphonyl chloride (1.7 g), pyridine (1.2 g) and 4-dimethylamino pyridine (100 mg).

The reaction mixture was refluxed for 14 h, cooled, washed with water (2×40 ml), dried (Na$_2$SO$_4$), filtered and concentrated to leave a reside. This was purified by chromatography on flash silica to give a colourless oil (4.5 g) which was dissolved in glacial acetic acid (50 ml) with anhydrous sodium acetate (1.6 g). The reaction mixture was heated at reflux for 24 h then concentrated to leave a residue which was dissolved in 75% agueous methanol (50 ml) and treated with potassium hydroxide (4 g). After 14 h the solvent was removed in vacuo and the residue partitioned between water (50 ml) and diethyl ether (3×50 ml). The combined organic layers were dried (Na$_2$SO$_4$) filtered and concentrated in vacuo. Chromatography of the residue on flash silica with 15% ethyl acetate in hexane as eluent gave the less polar isomer 3-bromo-5 -hydroxy-dibenzo[a,e]cyclooctene (0.8 g) as a colourless oil. δ (360 MHz, CDCl$_3$) 3.25 (1H, dd, J=14.1 and 9.7 Hz, CH$_A$H$_B$—CHOH), 3.48 (1H, dd, J =14.1 and 6.1 Hz, CH$_A$H$_B$—CHOH), 5.26 (1H, dd, J=9.7 and 6.1 Hz, CH$_A$H$_B$—CHOH), 6.75 (1H, d, J=12.3 Hz, CH$_C$=CH$_D$), 6.85 (1H, d, J=12.3 Hz, CH$_C$=CH$_D$), 6.94–7.28 (6H, m, ArH), 7.63 (1H, d, J =2 Hz, CH$_A$H$_B$—CH(OH)—C=CH—CBr=CH). m/e 302 and 300 (M+); and the more polar isomer 3-bromo-6-hydroxy-dibenzo[a,e]cyclooctene (0.26 g) as a colourless oil. δ (360 MHz, CDCl$_3$) 3.26 (1H, dd, J=13.9 and 10.1 Hz, CH$_A$H$_B$—CHOH), 3.42 (1H, dd, J =13.9 and 6.3 Hz, CH$_A$H$_B$—CHOH), 5.27 (1H, dd, J=10.1 and 6.3 Hz, CH$_A$H$_B$—CHOH), 6.73 (1H, d, J=12.3 Hz, CH$_C$=CH$_D$), 6.89 (1H, d, J=12.3 Hz CH$_C$=CH$_D$), 6.93–7.41 (7H, m, ArH). m/e 302 and 300 (M+).

Step D
3-Bromo-5-oxo-dibenzo[a,e]cyclooctene

To a solution of 3-bromo-5-hydroxy-dibenzo[a,e]cyclooctene (0.75 g) in dry dichloromethane (60 ml) was added pyridinium dichromate (2.1 g) and crushed 4 A molecular sieves (1.3 g). After stirring at room temperature for 14 h, diethyl ether (150 ml) was added and the reaction mixture was filtered through a plug of celite. The solvent was removed and the residue purified by chromatography on flash silica with 5% ethyl acetate in hexane as eluent to give, as a colorless solid, the title compound (0.7 g). δ(360 MHz, CDCl$_3$) 4.04 (2H, s, CH$_2$—C=O), 6.95 (1H, d, J=12.8 Hz, CH$_A$=CH$_B$), 7.09 (1H, d, J=12.8 Hz, CH$_A$=CH$_B$), 7.22–7.59 (6H, m, ArH), 8.36 (1H, d, J=2.2 Hz, C(O)—C=CH—CBr).

Step E
8-Bromo-I3-hydroxy-6-methyl-5,6,11,12-tetrahydrodibenzo[a,e]cycloocten-6,11-imine To a solution of 3-bromo-5-oxo-dibenzo[a,e]cyclooctene (0.68 g) in dry diethyl ether (30 ml) at 0° C. under an atmosphere of nitrogen was added methyl magnesium bromide (1.6 ml of a 3 molar solution in diethyl ether). After 2h at room temperature the reaction mixture was cooled to 0° C., quenched by the dropwise addition of saturated ammonium sulphate solution (20 ml) and extracted with diethyl ether (3×30 ml). The combined organic layers were dried (Na$_2$SO$_4$), filtered and evaporated to leave an oil which was dissolved in dry dichloromethane (10 ml) and added to a solution containing dichloroacetic acid (3.1 ml), sodium acetate (2.1 g) and hydroxylamine hydrochloride (1.75 g) in dichloromethane (40 ml), which had been prepared 2 hours previously. The reaction mixture was stirred at room temperature for 6h then refluxed for a further 6h. After cooling, 2N potassium hydroxide solution was added until the pH was 14 and the two phase mixture was stirred vigorously for 30 minutes. The organic layer was separated, washed with water (1×40 ml) and brine (1×40 ml), dried (Na$_2$SO$_4$) filtered and concentrated in vacuo. The crude residue was purified by chromatography on flash silica with 40% ethyl acetate in hexane as eluent, to give the title compound as a white foam (0.147 g). The nmr spectrum (360 MHz CDCl$_3$) showed a mixture of two atropisomers.

Step F
8-Bromo-6-methyl-5,6,11,12-tetrahydrodibenzo[a,e]cycloocten-6,11-imine hydrochloride To a solution of 8-bromo-13-hydroxy-6-methyl-5,6,11,12-tetrahydrodibenzo[a,e]cycloocten-6,11-imine (0.15 g) in glacial acetic acid (6 ml) was added zinc dust (0.3 g). The reaction mixture was heated at 65° C. under an inert atmosphere for 6h then filtered and concentrated to leave a residue which was partitioned between dichloromethane (30 ml) and dilute sodium hydroxide solution (30 ml). The organic layer was separated, dried (Na$_2$SO$_4$), filtered and evaporated in vacuo to leave a residue which was dissolved in 5 molar hydrogen chloride in ethyl acetate (20 ml). The solvent was evaporated to leave a solid which was recrystallised from ethyl acetate/diethyl ether. The title compound (0.055 g, m.p. 186°–189° C.) was collected by filtration and dried under high vacuum. δ(DMSO, 360 MHz) 1.89 (3H, s, CH$_3$), 3.13 (1H, d, J=16.5 Hz, PhCH$_A$H$_B$—C(NH) CH$_3$), 3.30 (1H, dd, J=16.6 and 5.0 Hz, PhCH$_C$H$_D$—C(NH)H$_E$), 3.68 (1H, d, J=16.6 Hz, PhCH$_C$H$_D$—C(NH)H$_E$), 3 82 (1H, d, J=16.5 Hz, PhCH$_A$H$_B$—C(NH)CH$_3$), 5.19 (1H, d, J=5.0 Hz, PhCH$_C$H$_C$—C(NH)H$_E$), 6.90–7.00 (4H, m, ArH), 7.22 (1H, d, J=8.0 Hz, C(NH)H$_E$—C=CH$_F$—CH$_G$=CBr—CH$_H$), 7.36 (1H, dd, J=8.0 and 1.7 Hz, C(NH)H$_E$—C=CH$_F$—CH$_G$=CBr—CH$_H$), 7 51 (1H, d J=1.7 Hz, C(NH)H$_E$—C=CH$_F$—CH$_G$=CBr—CH$_H$). n.O.e's observed from CH$_3$ to H$_H$ and H$_E$ to H$_F$.

EXAMPLE 7
5-Endo,6-dimethyl-5,6,11,12,-tetrahydrodibenzo[a,e]-cycloocten-6,11-imine acetate

Step A  5-Methyl-6-oxo-dibenzo[a,e]cyclooctene

To a stirred solution of disopropylamine (3.61 ml) in anhydrous tetrahydrofuran at 0° C. under nitrogen, was added a solution of n-butyllithium (8.72 ml of a 2.5M solution in hexane). The resulting solution was warmed to room temperature, then cooled to −60° C. and a solution of 5-oxo-dibenzo[a,e]cyclooctene (Example 1E, 4.0 g, 18 2 mmol) in anhydrous tetrahydrofuran (60 ml) added slowly. The reaction mixture was warmed to 0° C. then iodomethane (2.27 ml) added and the solution stirred at room temperature for 14h. The reaction was quenched with saturated ammonium sulphate solution (80 ml) and ammonium hydroxide solution (4M, 40 ml). After stirring for 30 minutes the reaction mixture was extracted with diethyl ether (1×50 ml), the ethereal layer was washed successively with water (4×20 ml) then brine (1×20 ml) and dried (Na$_2$SO$_4$). The solvent was removed in vacuo to give an oil which was separated by silica gel chromatography using 5% ethyl acetate in petroleum ether as eluent to give a colourless oil which was crystallised from hexane to give the title compound (0.91 g), mp 74°–76° C. δ (CDCl$_3$ 360 MHz,)

δ 1.62 (3H, d, CH-CH₃, J=6.7 Hz), 4.42 (1H, q, J=6.7 Hz, CH-CH₃), 7.08 (2H, s, CH=CH), 7.17-7.51 (7H, m, ArH), 8.31 (1H, dd, J=1.4 Hz and 8.1 Hz, ArH).

Step B
5-Hydroxy-5,6-dimethyl-dibenzo[a,e]cyclooct-11-ene

To a stirred solution of 5-methyl-6-oxo-dibenzo[a,e]cyclooctene (0.1 g) in anhydrous diethyl ether (10 ml) under nitrogen at 0° C. was added methyl lithium (0.43 ml of a 1.4 M solution in diethyl ether). After stirring for approximately 30 minutes water (10 ml) was added. The phases were separated and the ethereal layer was washed with water (2×10 ml), dried (Na₂SO₄) and the solvent removed in vacuo to give the title compound as a colourless solid (0.104 g), mP 86°-87° C. δ1.43 (CDCl₃ 360 MHz,) (3H, s, C—CH₃), 1.44 (3H, d, J=7.0 Hz, —CH—CH₃), 2.03 (1H, s, —OH), 4.07 (1H, q, J=7.0 Hz, —CH—CH₃), 6.75 (1H, d, J=11.8 Hz, CH_A=CH_B), 6.96-7.21 (8H, m, ArH and CH_A=CH_B), 7.41 (1H, d J=7.5 Hz, ArH), 7.85 (1H, d J=7.9 Hz, ArH) m/e 250 (M+).

Step C
13-Hydroxy-5-endo,6-dimethyl-5,6,11,12-tetrahydrodibenzo[a,e]cyclooctn-6,11-imine To a stirred solution of dichloroacetic acid (3.71 ml, 45 mmol) in dry dichloromethane (3.7 ml) at 0° C. was added anhydrous sodium acetate (2.46 g) and hydroxylamine hydrochloride (2.09 g). The resulting slurry was stirred at room temperature for 1.5h, additional dry dichloromethane (30 ml) was added, and after a further 1.5 h a solution of 5-hydroxy- 5,6-dimethyl-dibenzo[a,e]cyclooct-11-ene (750mg) in dry dichloromethane (8 ml) was introduced. The mixture was stirred at room temperature for 1 h, then trifluoroacetic acid (3.7 ml) added and the resulting solution stirred for a further 1.5h. The reaction was quenched with water (30 ml) and basified to pH 11 with concentrated ammonia solution. The phases were separated and the organic layer was washed with brine (10 ml) and dried over anhydrous sodium sulphate. Removal of the solvent gave a foam which was triturated with 20% ethyl acetate in petroleum ether to give, after filtration, the title compound (0.14 g), mp 124°-127° C. δ(CDCl₃ 360 MHz,)1.39 (3H, d, J=7.4 Hz, CH—CH₃), 1.62 (3H, s, C—CH₃), 2.56 (1H, dd. J=5.8 Hz and 15.5 Hz, H_ACH_B—CH_C), 4.28 (1H, q, J=7.4 Hz, CH—CH₃) 4.32 (1H, d, J=15.5 Hz, H ), 4.62 (1H, d, J=5.8 Hz, H_ACH_BCH_C), 6.9-7.1 (8H, m, ArH), m/e 265 (M+).

Step D
5-Endo,6-dimethyl-5,6,11,12-tetrahydrodibenzo[a,e]cycloocten-6 11-1mine acetate A mixture of 3-hydroxy-5,6-dimethyl-5,6,11,12-tetrahydrodibenzo[a,e]cycloocten-6,11-imine (0.5 g), zinc dust (75 mg) and glacial acetic acid (0.40 ml) was heated at 60°-65° C. under nitrogen for 26 hours. The mixture was then filtered, and the filtrate evaporated under vacuum to give an oil. This was partitioned between diethyl ether (10 ml) and concentrated ammonium hydroxide solution (10 ml) and the ethereal layer was washed with saturated brine (10 ml), then dried over anhydrous sodium sulphate. Removal of the solvent gave a solid which was triturated with diethyl ether to give the title compound (0.35 g) as the acetate salt, mp 112°-119° C. (dec). δ(CDCl₃ 360 MHz,) 1.47 (3H, d, J=7.5 Hz, CH—CH₃), 1.70 (3H, s, C—CH₃), 2.03 (3H, s, CH₃CO₂H), 3.11 (1H, dd, J=6.2 Hz and 15.5 Hz, H_ACH_B—CH_C), 3.55 (1H, q, J=7.5 Hz, CH—CH₃), 3.61 (1H, d, J=15.5 Hz, H_ACH_B-CH_C), 4.71 (1H, d, J=6.2 Hz, H_ACH_B—CH_C), 6 79-6.98 (8H, m, ArH), m/e 249 (M+).

EXAMPLE 8
Resolution of 6-methyl-5,6,11,12-tetrahydrodibenzo [a,e]cycloocten-6,11,-imine

Step A  Preparation of Diastereoisomers of N(L-Phenylalanyl)-6-methyl-5,6,11,12-tetrahydrodibenzo [a,e]cycloocten-6,11-imine To a solution of tert-butyloxycarbonyl-L-phenylalanine (0.397 g) in dry dichloromethane (5 ml) at 0° C. was added diisopropylethylamine (0.26 ml) and bis (2-oxo-oxazolidinyl) phosphinyl chloride (0.381 g) and the mixture stirred at 0° C. for ten minutes. A solution of 6-methyl-5,6,11,12-tetrahydrodibenzo [a,e]cycloocten-6.11-imine (0.350 g) in dichloromethane (2 ml) was added in one portion, followed by diisopropyl ethylamine (0.26 ml). The reaction mixture was allowed to warm to room temperature and stirred overnight. The solvents were evaporated and the residue partitioned between ethyl acetate (5 ml) and water (5 ml). The organic layer was washed with saturated aqueous sodium bicarbonate and water, then dried and evaporated to give a crude mixture of diastereoisomers of N-(tert-butoxy-L-phenylalanyl)-6-methyl-5,6,11,12-tetrahydrodibenzo[a e]-cycloocten-6,11-imine (0.350 g). To this crude mixture was added trifluoroacetic acid (2 ml) and the solution stirred for 15 minutes then evaporated to dryness. The residue was dissolved in ethyl acetate (5 ml) and water (5 ml) and 2N agueous sodium hydroxide (5 ml) were added. After shaking the aqueous layer was allowed to separate and was discarded. The organic layer was washed with water and brine, then dried and evaporated to give a crude mixture of diastereoisomers of N(L-phenylalanyl)-6-methyl-5,6,11,12-tetrahydrodibenzo[a,e]-cycloocten-6,11-imine. These were separated by chromatography on silica using 2% isopropyl alcohol in chloroform as eluent to give (i) Diastereoisomer A (95 mg). δ(CDCl₃, 360 MHz) 2.13 (3H, s, CH₃), 2.68 (1H, d, J=15.6 Hz), 2.87 (3H, m), 3.29 (1H, m), 3.94 (1H, m). 4.11 (1H, d, J=15.6 Hz), 5.45 (1H, m), 6.6-7.3 (13H, m, ArH); (ii) Diastereoisomer B (105 mg). δ(CDCl₃, 360 MHz), 2.08 (3H, s, CH₃), 2.86 (2H, m), 3 06 (2H, m), 3.55 (1H, d, J=15.7 Hz), 4.04 (1H, m), 4.22 (1H, d, J=16.0 Hz), 5.10 (1H, m), 6.77-7.25 (13H, ArH).

Step B°  Preparation of (+) 6-methyl-5,6,11,12-tetrahydrodibenzo[a,e]cycloocten-6,11-imine hydrochloride To a solution of diastereoisomer A (Step A, 90 mg) in ethyl alcohol (3 ml) was added diisopropyl ethylamine (96 µl) and phenyl isothiocyanate (74 µl) and the solution was stirred for 30 minutes. The solvents were evaporated and the residue dissolved in trifluoroacetic acid (2 ml), warmed to 40° C. and allowed to stand for 1 hr. The solvent was removed and the residue partitioned between ether (5 ml) and water (3 ml). The organic layer was discarded and the aqueous treated with 1N sodium hydroxide to pH 12 and extracted with ethyl acetate. The organic layer was washed with water, dried and evaporated to give crude (+) 6-methyl-5,6,11,12tetrahydrodibenzo[a,e]cycloocten-6,11-imine which was purified by column chromatography using 5% methanol in chloroform as eluent. This product was dissolved in a little ethyl acetate and treated with 5M hydrogen chloride in ethyl acetate to give the hydrochloride salt, which was freeze dried from water, to give (+)-6-methyl-5,6,11,12-tetrahydrodibenzo[a,e]-cycloocten-6,11-imine hydrochloride (36 mg) mp 280°-285° C. The $^1$H nmr spectrum was identical with the racemate (Example II).

Step C Preparation of
(-)-6-methyl-5,6,11,12-tetrahydrodibenzo[a,e]cycloocten-6,11-imine hydrochloride Using the above procedure (Step B) diastereoisomer B (Step A, 100 mg) for diastereoisomer A gave (−)-6-methyl-5,6,11,12-tetrahydrodibenzo [a,e]-cycloocten-6,11-imine hydrochloride (50 mg), mp 282°-285° C. The $^1$H nmr spectrum was identical with the racemate (Example II).

EXAMPLE 9

6-Methyl-11-n-butyl-5,6,11,12-tetrahydrodibenzo[a,e]-cycloocten-6,11-imine hydrochloride Step A preparation of
6-methoxylamino-6-methyl-5,6-dihydrodibenzo[a,e]cyclooctene To a solution of dichloroacetic acid (19.4 g) in dry dichloromethane (25 ml) was added anhydrous sodium acetate (8.2 g) with cooling and stirring. The mixture was stirred until the solid had completely dissolved, then a further 15 ml dichloromethane was added followed by methoxylamine hydrochloride (8.35 g). After 30 mins stirring a solution of 6-methyl-6-hydroxy-5,6-dihydrodibenzo[a,e]cyclooctene (2.36 g) in dichloromethane (10 ml) was added and the mixture stirred at room temperature for 4 hours. The mixture was cooled in ice treated with 2N sodium hydroxide to pH 12 and the organic layer separated, washed with water, dried and evaporated to give a clear oil. This was chromatographed on silica using 20% ethyl acetate/in hexane as eluent to give 6-methoxylamine-6-methyl-5,6-dihydrodibenzo[a,e]cyclooctene (2.21 g). mp 48°-50° C.

Step B Preparation of
N-methoxy-6-methyl-5,6,11,12-tetrahydrodibenzo[a,e]-cycloocten-6,11-imine To a solution of the product from Step A (1.90 g) in 1:9 dimethylsulfoxide/toluene (20 ml) at room temperature was added potassium tert-butoxide (0.80 g) in one portion. The suspension was warmed to 55° C. with stirring for 3 minutes under nitrogen. The mixture was cooled, diluted with one volume of diethyl ether washed with water (3×20 ml), dried and evaporated. Crystallisation from ether/hexane gave N-methoxy-6-methyl-5,6,11,12-tetrahydrodibenzo [a,e]cycloocten-6,11-imine (1.28 g). mp 85°-88° C.

Step C Preparation of
6-methyl-11-n-butyl-5,6,11,12-tetrahyorodibenzo[a,e]-cycloocten-6,11-imine hydrochloride To a solution of the product from Step B (0.132 g) in anhydrous ether (3 ml) under nitrogen at −78° C. was added a solution of n-butyl lithium (0.3 ml of a 1.47M solution in hexane). The solution was allowed to warm to room temperature and stirred for 4 hrs. Water (2 ml) was cautiously added and the aqueous layer separated and discarded. The organic layer was dried and evaporated, then chromatographed on silica using 1:1 ethyl acetate/hexane as eluent. Further chromatography using 1:4 ethyl acetate/hexane as eluent afforded pure 6-methyl-11-n-butyl-5,6,11,12tetrahydrodibenzo[a,e]-cycloocten-6,11-imine (0.046 g). This was dissolved in ethyl acetate (1 ml) and 5M hydrogen chloride in ethyl acetate (0.5 ml) was added. Evaporation and trituration with ether gave the required 6-methyl-11-n-butyl-5,6,11,12-tetrahydrodibenzo[a,e]cycloocten-6,11-imine hydrochloride (0.045 g), mp 230°-234° C.

EXAMPLE 10

3-Bromo-6-methyl-5,6,11,12-tetrahydrodibenzo[a,e]-cycloocten-6,11-imine hydrochloride Step A  3-Bromo-6-oxo-dibenzo[a,e]cyclooctene To a solution of 3-bromo-6-hydroxy-dibenzo[a,e]-cyclooctene (Example 6C) (2 g) in dry dichloromethane (60 ml) was added pyridinium dichromate (4.9 g) and crushed 4A molecular sieves (3.2 g). After stirring at room temperature for 5h, diethyl ether (100 ml) was added and the reaction mixture was filtered through a plug of celite. The solvent was removed in vacuo and the residue then dissolved in dichloromethane (100 ml), washed with water (100 ml), dried (Na$_2$SO$_4$), filtered and concentrated in vacuo to give the title compound as an oil (1.6 g). δ (360 MHz, CDCl$_3$) 4.04 (2H, s, CH$_2$—C=O), 6.95 (1H, d, J=12.8 Hz, ArCH$_a$=CH-$_B$Ar), 7.08 (1H, d, J=12.8 Hz, ArCH$_A$=CH$_B$Ar), 7.23-7.53 (6H, m, aromatics) and 8.19 (1H, d, J=8.2 Hz, C(O)—C=CH—CH=CH—CH). m/e 300 and 298 (M+).

Step B
3-Bromo-13-hydroxy-6-methyl-5,6,11,12-tetrahydrodibenzo[a,e]cyloocten-6 11-imine To a solution of 3-bromo-6-oxo-dibenzo[a,e]cyclooctene (1.5 g) in dry diethyl ether (50 ml) at 0° C. under an atmosphere of nitrogen was added methyl magnesium bromide (5.0 ml of a 3 molar solution). After 4h at room temperature the reaction mixture was cooled to 0° C., quenched by the dropwise addition of saturated ammonium sulphate solution (30 ml) and extracted into diethyl ether (3×50 ml). The combined organic layers were dried (Na$_2$SO$_4$), filtered and evaporated to leave an oil (1.6 g) which was dissolved in dry dichloromethane (12 ml) and added to a solution containing dichloroacetic acid (6.3 ml), sodium acetate (4.1 g), and hydroxylamine hydrochloride (3.47 g) in dichloromethane (40 ml) which had been prepared 3 hours previously. The reaction mixture was stirred at room temperature for 14h and then refluxed for a further 7h. After cooling, 2N potassium hydroxide solution was added until the pH was 14 and the two phase mixture was stirred vigorously for 30 minutes. The organic layer was separated, washed with water (1×60 ml) and then brine (1×60 ml), dried (Na$_2$SO$_4$), filtered and concentrated in vacuo. The crude residue was purified by chromatography on flash silica with 15% ethyl acetate in dichloromethane as eluent to give the title compound (0.195 g), m.p.171°-176° C. The NMR spectrum (360 MHz, CDCl$_3$) showed a mixture of two atropisomers. m/e 331 and 329(M+).

Step C
3-Bromo-6-methyl-5,6,11,12-tetrahydrodibenzo[a,e]-cycloocten-6,11-imine hydrochloride To a solution of 3-bromo-13-hydroxy-6-methyl-5,6,11,12-tetrahydro-dibenzo[a,e]cycloocten-6,11-imine (0.190 g) in glacial acetic acid (10 ml) was added zinc dust (0.40 g). The reaction mixture was heated at 65° C. under an atmosphere of nitrogen for 6h then filtered and concentrated in vacuo to leave a residue which was partitioned between dichloromethane (50 ml) and 1N sodium hydroxide solution (50 ml). The organic layer was separated, dried ($Na_2SO_4$ filtered and evaporated to leave a residue which was dissolved in 5 molar hydrogen chloride in ethyl acetate (10 ml).

The solvent was evaporated to leave solid which was recrystallised from ethyl acetate-diethyl ether. The title compound was collected by filtration and dried under high vacuum (0.047 g), m.p. 274° C. 67 (360 MHz) 2.15 (3H, s, $CH_3$), 2.85 (1H, d, J=16.5 Hz, $CH_AH_B$—C($CH_3$)), 3.16 (1H, dd, J=16.8 and 5.2 Hz, $CH_CH_D$—$CH_ENH$), 4 12 (1H d, J=16.8 Hz, $CH_CH_D$—$CH_ENH$), 4.32 (1H, d, J=16.5 Hz, $CH_AH_B$—C($CH_3$)), 5.30 (1H, d, J=5.2 Hz, $CH_CH_D$—$CH_ENH$), 6.73 (1H, d, J=8.1 Hz, $CH_F$=CH $CH_G$—C(Br)=$CH_H$), 6.96 (1H, d, J=1.9 Hz, $CH_F$=$CH_G$—C(Br)=$CH_H$), and 7.03–7,21 (5H, m, aromatics). Irradiation of $H_D$ ($\delta$4.1) gave a n.O.e to $H_F$ ($\delta$6.73) and irradiation or $H_B$ ($\delta$4 32) gave a n.O.e to $H_H$ ($\delta$6.96). m/e, found 313.0442; $C_{17}H_{16}NBr$ requires 313.0466. Found C, 56.9; H,5.0; N,3.90. $C_{17}H_{17}NBr \cdot HCl \cdot 0.5H_2O$ requires C, 56.8; H, 5.0; N, 3.90%.

EXAMPLE 11

10-Chloro-6-methyl-5,6,11,12-tetrahydrodibenzo[a,e]cycloocten-6,11-imine hydrochloride

Step A
1-Chloro-5-methylene-dibenzo[a,d]cycloheptene

A solution of 1-chloro-dibenzo[a,d]cyclohepten-5-one (13.0 g) in anhydrous tetrahydrofuran (80.0 ml) was cooled to 0° C. and methyllithium (35.5 ml of a 1.6 molar solution) was added by syringe. After 1h, water (60 ml) was added dropwise and the reaction mixture extracted with diethyl ether (3×100 ml). The combined organic layers were dried over sodium sulphate, filtered and concentrated in vacuo to give a pale yellow oil (13.02 g). This was dissolved in dry dichloromethane (80 ml) with dichloroacetic acid (2.5 ml) and refluxed for 9h. The mixture was cooled, washed with saturated sodium hydrogen carbonate solution (1×120 ml) and brine (1×120 ml), dried ($Na_2SO_4$), filtered and concentrated in vacuo to give the title compound as an oil (9.1 g). $\delta$(360 MHz, $CDCl_3$) 5.25 (1H, d, J=1.4 Hz, $CH_AH_B$), 5.26 (1H, d, J=1.4 Hz, $CH_AH_B$), 6.98 (1H, d, J=11.8 Hz, ArCH$_C$=CH$_D$Ar), 7.20 (1H, d, J=11.8 Hz, ArCH$_C$=CH$_D$Ar) and 7.20–7.38 (7H, m, aromatics). m/e 238 (M+).

Step B  1-Chloro-5-hydroxymethyl-dibenzo[a,d]cycloheptene

To a solution of 1-chloro-5-methylene-dibenzo[a,d]cycloheptene (9.0 g) in dry tetrahydrofuran (60 ml), under an inert atmosphere was added 9-borabicyclo[3,3,1]nonane (80.5 ml of a 0.5 molar solution in THF) at ambient temperature and the reaction mixture was then refluxed for 3h. After cooling, the reaction was quenched by the slow addition of 2N sodium hydroxide solution (180 ml) and 30% hydrogen peroxide (36 ml). After stirring vigorously at 0° C. for 45 minutes the reaction mixture was allowed to warm to room temperature over a 2h period then extracted into diethyl ether (3×250 ml). The combined organic layers were washed with brine (1×500 ml), dried ($Na_2SO_4$), filtered and concentrated in vacuo to leave a residue which was purified by chromatography on flash silica with 40% ethyl acetate in hexane as eluent to give the title compound (8.3 g) as a colourless oil. $\delta$ (360 MHz, $CDCl_3$) 3.87 (2H, m, CH—$CH_2OH$), 4.21 (1H, t, J=7.9 Hz, CH—$CH_2OH$) 7.02 (1H, d, J=11.9 Hz, $CH_A$=$CH_B$) and 7.17–7.46 (8H, m, $CH_A$=$CH_B$ and 7 aromatic protons). m/e 258 and 256 (M+).

Step C  1-Chloro-5-hydroxy-dibenzo[a,e]cyclooctene and 1-Chloro-6-hydroxy-dibenzo[a,e]cyclooctene To a solution of 1-chloro-5-hydroxymethyl-dibenzo[a,d]cycloheptene (8.3 g) in dichloromethane (80 ml) was added p-toluenesulphonyl chloride (6.3 g), pyridine (5.11 g), and 4-dimethylamino pyridine (150 mg). The reaction mixture was refluxed for 15h, cooled washed with water (2×80 ml), dried ($Na_2SO_4$), filtered and concentrated in vacuo to leave an oil which was purified by chromatography on flash silica with 15% ethyl acetate in hexane as eluent. The purified tosylate was dissolved in glacial acetic acid (100 ml) with anhydrous sodium acetate (4.4 g) and the solution refluxed for 15h. The mixture was concentrated in vacuo to leave a residue which was partitioned between dichloromethane (3×100 ml) and water (100 ml). The combined organic layers were dried ($Na_2SO_4$), filtered and concentrated in vacuo to leave a residue which was dissolved in 75% aqueous methanol (160 ml) and treated at 0° C. with potassium hydroxide (10 g). After 14h the reaction mixture was concentrated in vacuo. Chromatography of the residue on flash silica with 15% ethyl acetate in hexane as eluent gave the less polar isomer, 1-chloro-5-hydroxydibenzo[a,e]cyclooctene (1.5 g), m.p. 158°–160° C. $\delta$(360 MHz, $CDCl_3$) 3.12 (1H, dd, J =1.51 and 10.2 Hz, $CH_AH_B$—CHOH), 3.63 (1H, dd, J=15.1 and 6.9 Hz, $CH_AH_B$—CHOH), 5.57 (1H, dd, J=10.2 and 6.9 Hz, $CH_AH_B$—CHOH), 6.74 (1H, d, J=11.9 Hz, ArCH$_D$=CH$_E$—Ar), 7.03 (1H, d, J=11.9 Hz, ArCH$_D$=CH$_E$Ar) and 7.07–7.46 (7H, m, aromatics). m/e 256 (M+). i.r.($\nu_{max}$, nujol) 3350–3100 $cm^{-1}$ (br, OH). Found: C, 74.5; H, 5.1. $C_{16}H_{13}C_{10}$ requires: C, 74.9; H, 5.1%. Further elution gave the more polar isomer, 1-chloro-6-hydroxy-dibenzo[a,e]cyclooctene (0.47 g), m.p. 144°–146° C. $\delta$(360 MHz, $CDCl_3$) 3.39 (2H, m, CH—CHOH), 5.13 (1H, m, $CH_2$—CHOH), 6.77 (1H, d, J=11.9 Hz, Ar—$CH_A$=$CH_B$), 7.02 (1H, d, J=11.9 Hz, ArCH$_A$=CH$_B$) and 7.07–7.38 (7H, m, aromatics). m/e 256 (M+). i.r ($\nu_{max}$, nujol) 3300–3100 $cm^{-1}$ (br, OH). Found: C, 74.8; H, 5.2. $C_{16}H_{13}C_{10}$ requires: C, 74.9; H, 5.1%.

Step D  1-Chloro-5-oxo-dibenzo[a,e]cyclooctene

To a solution of 1-chloro-5-hydroxy-dibenzo[a,e]cyclooctene (1.5 g) in dry dichloromethane (60 ml) was added pyridinium dichromate (5.0 g) and crushed 4A molecular sieves (2.5 g). After stirring at room temperature for 3h. diethyl ether (150 ml) was added and the reaction mixture was filtered through a plug of celite. The solvent was removed in vacuo and the residue purified by chromatography on flash silica with 10% ethyl acetate in hexane as eluent to give the title compound (1.35 g) m.p. 151°–153° C. $\delta$(360 MHz, $CDCl_3$) 4.09 (2H, s, $CH_2$—C=O). 7.06 (1H, d, J=11.9 Hz, Ar-CH$_A$=CH$_B$Ar), 7.18 (1H, d, J=11.9 Hz, ArCH$_A$=CH$_B$Ar), 7.20–7.30 (5H, m, aromatics), 7.50 (1H, dd, J=7.8 and 1.4 Hz, CH=CCl) and 7.86 (1H, dd, J=8.0 and 1.3 Hz, CH=C—C=O). m/e 254 (M+). i.r. ($\nu_{max}$, nujol)

1670 cm$^{-1}$ (CO). Found: C, 75.1; H, 4.6. C$_{16}$H$_{11}$C1O requires: C, 75.4; H, 4.4%.

Step E
10-Chloro-13-hydroxy-6-methyl-5,6,11,12-tetrahydrodibenzo[a,e]cyxclooctene-6-,11-imine To a solution of 1-chloro-5-oxo-dibenzo[a,e]cyclooctene (1.3 g) in dry diethyl ether (60.0 ml) at 0° C. under an atmosphere of nitrogen was added methyl magnesium bromide (4.0 ml of a 3 molar solution). After 3h at room temperature the mixture was cooled to 0° C., quenched dropwise with saturated ammonium sulphate solution (20.0 ml) and extracted with diethyl ether (3×50 ml). The combined organic layers were dried (Na$_2$SO$_4$), filtered and evaporated to leave an oil (1.1 g). which was dissolved in dry dichloromethane (15 ml) and added to a solution containing dichloroacetic acid (5.6 ml), sodium acetate (3.69 g) and hydroxylamine hydrochloride (3.12 g) in dichloromethane (40 ml). The reaction mixture was stirred at room temperature for two hours then refluxed for a further 24h. After cooling, 2N potassium hydroxide solution was added until the pH was 14 and the two phase mixture was stirred vigorously for 30 minutes. The organic layer was separated, washed with water 1×50 ml) and brine (1×50 ml), dried (Na$_2$SO$_4$), filtered and concentrated in vacuo. The crude product was purified by chromatography using flash silica with 5% ethyl acetate in dichloromethane as eluent to give the title compound (0.13 g), m.p. 162°–164° C. The NMR spectrum (360 MHz, CDCl$_3$) showed a mixture of two atropisomers. m/e 287 and 285 (M+).

Step F
10-Chloro-6-methyl-5,6,11,12-tetrahydrodibenzo[a,e]-cyclooctene-6,11-imine hydrochloride To a solution of 10-chloro-13-hydroxy-6-methyl-5,6,11,12-tetrahydrodibenzo[a,e]cyclooctene-6.11-imino (0.13 g) in glacial acetic acid (5 ml) was added zinc dust (0.26 g). The reaction mixture was heated at 70° C. for 8h, then cooled, filtered and concentrated in vacuo to leave a residue which was partitioned between dichloromethane (30 ml) and dilute sodium hydroxide solution (30 ml). The organic layer was separated, dried (Na$_2$SO$_4$), filtered and concentrated in vacuo. The residue was purified by chromatography using flash silica with 3% methanol in dichloromethane as eluent. The product was dissolved in 5 molar hydrogen chloride in ethyl acetate (15 ml) and the solvent was evaporated to give the title compound (0.06 g), m.p. 196°–198° C. δ(360 MHz, DMSO) 1.91 (3H, s, CH$_3$), 3.09 (1H, d, J=16.4 Hz, C$\underline{H}_A$H$_B$—(CH$_3$)), 3.35 (1H, dd, J=16.7 and 5.1Hz, CH$_C$$\underline{H}_D$—CH$_E$NH), 3.78 (1H, d, J=16.7 Hz, CH$_C$$\underline{H}_D$—CH$_E$NH), 3.95 (1H, d, J=16.4 Hz, CH$_A$$\underline{H}_B$—C(CH$_3$)), 5.26 (1H, d, J=5.1 Hz) and 6.87-7.24 (7H, m, aromatics). Irradiation of H$_E$ (δ5.26) gave no n.o.e to the aromatic protons and irradiation of H$_C$ (δ3.35) did give a n.O.e to the aromatic protons. m/e, Found: 269. 0968, C$_{17}$H$_{16}$C1N requires: 269. 0971. Found: C, 64.4; H, 5.6; N, 4.3. C$_{17}$H$_{13}$C1N.HCl.0.5H$_2$O requires: C, 64.8; H, 5.8; N, 4.4%.

EXAMPLE 12
2-Methoxy-6-methyl-5,6,11,12-tetrahydrodibenzo[a,e]cycloocten-6,11-imine hydrochloride Step A
2-Methoxy-5-methylene-dibenzo[a,d]cycloheptene A solution of 2-methoxy-dibenzo[a,d]cyclohepten-5-one (20 g) in anhydrous tetrahydrofuran (200 ml) was cooled to 0° C. and methyllithium (55.8 ml of a 1.6 molar solution) was added by syringe. After 45 minutes, water (70 ml) was added dropwise and the reaction mixture extracted with diethyl ether (3×100 ml). The combined organic phases were dried over sodium sulphate, filtered and concentrated in vacuo to give a colourless oil (18.8 g). This was dissolved in dichloromethane (120 ml) with dichloroacetic acid (2.5 ml) and stirred at room temperature for 2h, washed with saturated sodium hydrogen carbonate solution (100 ml), dried (Na$_2$SO$_4$), filtered and concentrated in vacuo. The residue was purified by chromatography using flash silica with 5% ethyl acetate in hexane as eluent to give the title compound as a colourless solid (12.95 g, m.p. 131°–133° C.). δ(360 MHz, CDCl$_3$) 3.8 (3H, s, OCH$_3$), 5.21 (2H, 2d, J=1.95 Hz, =CH$_2$), δ6.75 (1H, d, J=11.8 Hz, Ar—C$\underline{H}_A$=CH$_B$Ar), 6.76 (1H, d, J=2.7 Hz, C$\underline{H}$=(COCH$_3$)—CH), 6.90 (1H, dd, J=8.6 and 2.7 Hz, C$\overline{\underline{H}}$=C(COCH$_3$)—C$\underline{H}$) and 7.23-7.40 (5H, m, aromatics). m/e 234 (M+).

Step B
2-Methoxy-5-hydroxymethyl-dibenzo[a,d]cycloheptene

To a solution of 2-methoxy-5-methylene-dibenzo [a,d]cycloheptene (12.8 g) in dry THF (50 ml), under an inert atmosphere, was added 9-borabicyclo[3,3,1]nonane (116 ml of a 0.5 molar solution in THF) at ambient temperature, and the reaction mixture was then refluxed for 3h. After cooling in an ice bath the reaction was quenched by the slow addition of 2N sodium hydroxide solution (150 ml) and 30% hydrogen peroxide (30 ml). After stirring vigorously at 0° C. for 45 minutes the reaction mixture was allowed to warm to room temperature over a period of 2h then extracted with diethyl ether (3×200 ml). The combined organic layers were washed with brine (1×300 ml), dried (Na$_2$SO$_4$), filtered and concentrated in vacuo to leave a residue, which was purified by chromatography on flash silica with 30% ethyl acetate in hexane as eluent, to give the title compound (10.9 g) as an oil. δ(360 MHz, CDCl$_3$) 3.77–3.81 (2H, d, J=8.1 Hz, CH$_2$), 3.80 (3H, s, OCH$_3$), 4.16 (1H, t. J=8.1 Hz, CH—CH$_2$OH), 6.79 (1H, d, J=11.9 Hz, ArC$\underline{H}_A$=CH$_B$—Ar), 6.33 (1H, d, J=2.6 Hz, C$\underline{H}$=C(OCH$_3$)—CH), 6.85 (1H, d, J=11.9 Hz, Ar—C$\overline{\underline{H}}_A$=CH$_B$—Ar), 6.89 (1H, dd, J=8.3 and 2.6 Hz, CH=C($\overline{O}$CH$_3$)C$\underline{H}$) and 7.23-7.33 (5H, m, aromatics). m/e (CI+) 253 ($\overline{M}$+1).

Step C
2-Methoxy-5-p-toluenesulphonyloxymethyldibenzo[a,d]cycloheptene

To a solution of 2-methoxy-5-hydroxymethyldibenzo[a,d]cycloheptene (10.5 g) in dry dichloromethane (150 ml) was added p-toluenesulphonyl chloride (8.1 g), pyridine (6.6 g) and 4-dimethylamino pyridine (300 mg). The reaction mixture was refluxed for 15h, cooled, washed with water (2×200 ml), dried (Na$_2$SO$_4$), filtered and concentrated in vacuo. The residue was purified by flash silica chromatography using 15% ethyl acetate in hexane as eluent to give the title compound as an oil (13.5 g). δ(360 MHz, CDCl$_3$), 2.44 (3H, s, Ar—CH$_3$), 3.78 (3H, s, OCH$_3$), 4.19-4.31 (3H, m CH-CH$_2$—OSO$_2$Ar). 6.58 (1H, d, J=11.9 Hz, Ar—C$\overline{H}$=CH—Ar), 6.65 (1H, d, J=11.9 Hz, Ar—C$\overline{H}$=CH—Ar), 6.68 (1H, d, J=2.7, CH=C(OC$\overline{H}_3$)—CH), 6.85 (1H, dd, J=8.4 and 2.7 Hz, CH=C(OCH$_3$)—CH) and 7.16-7.42 (9H, m, aromatics). m/e 406 (M+).

Step D
2-Methoxy-5-hydroxy-dibenzo[a,e]cyclooctene and 2-Methoxy-6-hydroxy-dibenzo[a,e]cyclooctene To a solution of 2-methoxy-5-p-toluenesulphonyloxymethyldibenzo[a,d]cycloheptene (13.5 g) in glacial acetic acid (100 ml) was added anhydrous sodium acetate (5.6 g). The reaction mixture was heated under reflux for 15h then the solvent was removed under vacuum to leave a residue which was partitioned between dichloromethane (3×120 ml) and water (120 ml). The combined organic layers were dried (Na$_2$SO$_4$), filtered and concentrated in vacuo to leave a residue which was dissolved in 75% aqueous methanol (100 ml) and treated with potassium hydroxide at 0° C. until the pH was approximately 12. After 3h the reaction mixture was concentrated in vacuo and the presidue partitioned between water (100 ml) and diethyl ether (3100 ml). The combined organic layers were dried (Na$_2$SO$_4$). filtered and concentrated in vacuo. Chromatography of the residue on flash silica with 10% ethyl acetate in hexane as eluent initially gave the less polar isomer, 2-methoxy-6-hydroxy-dibenzo [c,e]cyclooctene (1.6 g), m.p. 97°-99° C. δ (360 MHz, CDCl$_3$) 3.25 (1H. dd, J=13.8 and 10.0 Hz, CH$_A$H$_B$—CH$_C$OH), 3.39 (1H, dd, J=13.8 and 6.2 Hz, $\overline{CH_AH_B}$CH$_C$OH), 3.72 (3H, s, OCH$_3$), 5.23 (1H, dd, J=10.0 and 6.2 Hz, CH$_A$H$_B$—CH$_C$—OH), 6.61 (1H, d, J=2.7 Hz, CH=C(OC$\overline{H}_3$)—CH=CH), 6.70 (1H, dd, J=8.4 and 2.7 Hz, CH=$\overline{C}$(OCH$_3$)—CH=CH), 6.77 (1H, d, J=11.9, ArCH=CH—Ar), $\overline{6.87}$ (1H, d, J=11.9 Hz, Ar—CH=CH—Ar), 7.09-7.21 (3H, m aromatics), 7.16 (1H, dd, J=8.5 and 2.7 Hz, CH=C(OCH$_3$)—CH=CH) and 7.44 (1H, dd, J=8.6 and 2.7 Hz, C$\overline{H}$=C—CH$_2$OH). Irradiation of H$_B$ (δ3.39) gave a n.o.e to the proton at δ7.16 which is on the same ring as the methoxy group and irradiation of H$_C$ (δ5.23) gave a n.o.e to the proton at δ7.45 which is on the other aromatic ring. m/e 252 (M+). i.r. ($\nu_{max}$ nujol mull) 3400-3100 cm$^{-1}$ (br, OH). Found: C, 78.8; H, 6.5. C$_{17}$H$_{16}$O$_2$.0.35 H$_2$O requires: C, 78.9; H, 6.5%. The more polar product next obtained, as an oil, was 2-methoxy-5-hydroxymethyldibenzo[a,d]cycloheptene (5.2 g, 62%). 2-Methoxy-5-hydroxydibenzo[a,e]cyclooctene was not isolated.

Step E  2-Methoxy-6-oxo-dibenzo[a,e]cyclooctene

To a solution of 2-methoxy-6-hydroxy-dibenzo[a,e]cyclooctene (1.5 g) in dry dichloromethane (100 ml) was added pyridinium dichromate (4.5 g) and crushed 4A molecular sieves (2.3 g). After stirring at room temperature for 2h, diethyl ether (200 ml) was added and the reaction mixture was filtered through a plug of celite. The solvent was removed in vacuo and the residue purified by chromatography on flash silica with 5% ethyl acetate in hexane as eluent to give, as a colourless solid, the title compound (1.4 g), m.p. 104°-106° C. δ(360 MHz, CDCl$_3$), 3.75 (3H, s, CH$_3$O), 3.99 (2H, s, CH$_2$—CO), 6.73 (1H, d, J=2.7 Hz, C$\overline{H}$=(OCH$_3$)—CH), 6.86 (1H, dd, J=8.5 and 2.7 Hz, CH=C(OCH$_3$)—CH), 7.01 (2H, s, Ar—CH=CH—Ar), 7.29-7.51 (4H, m, aromatics) and 8.24 ($\overline{1H}$, dd, J=8.0 and 1.4 Hz, CH=C—CO). m/e 250 (M+). i.r. ($\nu_{max}$, nujol) 1665 cm$^{-1}$(CO). Found: C,81.5; H, 5.6. C$_{17}$H$_{14}$O$_2$ requires: C, 81.0; H, 5.8%

Step F
2-Methoxy-13-hydroxy-6-methyl-5,6,11,12-tetrahydrodibenzo[a,e]cycloocten-6,11-imine To a solution of 2-methoxy-6-oxo-dibenzo[a,e]cyclooctene (1.4 g) in dry diethyl ether (60.0 ml) at 0° C. under an atmosphere of nitrogen was added methyl magnesium bromide (3.7 ml of a 3 molar solution). After 45 minutes at 0° C. the reaction mixture was quenched by the dropwise addition of saturated ammonium sulphate solution (25 ml) and extracted into diethyl ether (3×50 ml). The combined organic layers were dried (Na$_2$SO$_4$), filtered and evaporated to leave an oil (1.3 g) which was dissolved in dry dichloromethane (10 ml) and added to a solution containing dichloroacetic acid (7 ml), sodium acetate (4.6 g) and hydroxylamine hydrohloride (3.9 g) in dichloromethane (37 ml) which had been prepared 3h previously. The reaction mixture was stirred at room temperature for 8h. After cooling, 2N potassium hydroxide solution was added until the pH was 14 and the two phase mixture was stirred vigorously for 30 minutes. The organic layer was separated, washed with water (60 ml) and brine (60 ml), dried (Na$_2$SO$_4$), filtered and concentrated in vacuo. The crude residue was purified by chromatography on flash silica with 20% ethyl acetate in hexane to give, as a colourless solid, the title compound (0 8 g), m.p. 185°-197° C. The NMR spectrum showed a 2:1 mixture of atropisomers (360 MHz, CDCl$_3$); major isomer: δ1.62 (3H, s, CH$_3$), 2.37 (1H, d, J=15.8 Hz, CH$_A$H$_B$—C(CH$_3$), 2.55 (1H, dd, J=16.0 and 5.2 Hz, CH$_C$H$_D$—CH$_E$NOH), 4.04 (1H, d, J=15.8, CH$_A$H$_B$—C(CH$_3$)), 4.2 (1H, d, J=16.0 Hz, CH$_C$H$_D$—CH$_E$NOH), 4.64 (1H, d, J=5.2 Hz, CH$_A$H$_B$—CH$_E$NOH) and 6.36-7.08 (7H, m, aromatics); minor isomer: δ1.75 (3H, s, CH$_3$), 2.82 (1H, d, J=15.5 Hz, CH$_A$H$_B$—C(CH$_3$)), 3.03 (1H, dd, J=16.0 and 7.2 Hz, C$\overline{H}_C$H$_D$—CH$_E$NOH), 3.36 (1H, d, J=15.5 Hz, CH$_A$H$_B$—C(C$_3$)), 3.55 (1H, d, J=16.0 Hz, CH$_C$H$_D$—CH$_E$NOH), 4.73 (1H, d, J=7.2 Hz, CH$_C$H$_D$—CH$_E$NOH), 6.36-7.08 (7H, m, aromatics). m/e 281 ($\overline{M}^+$). Found: C, 75.8: H, 6.9; N, 4.8. C$_{18}$H$_{19}$NO$_2$.0.25 H$_2$O requires: C,75.6: H, 6.9; N, 4.9%.

Step G
2-Methoxy-6-methyl-5,6,11,12-tetrahydrodibenzo[a,e]cycloocten-6,11-imine hydrochloride To a solution of 2-methoxy-13-hydroxy-6-methyl-5,6,11,12-tetrahydrodibenzo[a,e]cycloocten-6,11-imine (0.8 g) in glacial acetic acid (20 ml) was added zinc dust (1.6 g). The reaction mixture was heated at 65° C. under an atmosphere of nitrogen. After 6h the mixture mixture was filtered and concentrated in vacuo to leave a residue which was partitioned between dichloromethane (50 ml) and dilute sodium hydroxide solution (50 ml). The organic layer was separated, dried (Na$_2$SO$_4$), filtered and evaporated to leave a residue which was dissolved in 5 molar hydrogen chloride in ethyl acetate (25 ml). The solvent was evaporated to leave a solid which was recrystallised from methanol/ethyl acetate/diethyl ether. The title compound (290 mg), m.p. 229°-231° C., was collected by filtration and dried under high vacuum. δ(360 MHz, DMSO) 1.87 (3H, s, CH₃), 3.04 (1H, d, J=16.4 Hz, CH$_A$H$_B$—C(CH₃)), 3.24 (1H, dd, J=16.8 and 5.2 Hz, CH$_C\overline{H}_D$—CH$_E$NOH), 3.76 (1H, d, J=16.4 Hz, CH$_A\overline{H}_B$—C(CH₃)), 5.15 (1H, d, J=5.2 Hz, CH$_C\overline{H}_D$—C$\overline{H}_E$NOH), 6.49 (2H, m, C$\overline{H}_F$=C(OCH₃)—CH$_G$=CH$_H$), 6.79 (1H, d, J=8.7 Hz, CH$_F$=C(OCH₃)—CH$_G$=C$\overline{H}_H$), 7.16–7.26 (4H, m, aromatics) and 10.22–10.40 (2H, m, NH₂). Irradiation of H (δ6.79) gave a n.o.e to H$_A$ (δ3.04) and irradiation of the multiplet at δ6.49 (H$_F$ and H$_G$) gave a n.o.e to H$_C$ (δ3.24). m/e 265 (M+); Found: 265.1444; C₁₈H₁₉NO requires: 265.1466. Found: C, 70.31; H, 6.70; N, 4.50. C₁₈H₁₉NO.HCl.H₂O requires: C, 70.37; H, 6.75; N, 4.56%.

EXAMPLE 13

2-Hydroxy-6-methyl-5,6,11,12-tetrahydrodibenzo[a,e]-cycloocten-6,11-imine hydrochloride To a solution of 2-methoxy-6-methyl-5,6,11,12-tetrahydrodibenzo[a,e]cycloocten-6,11-imine (0.2 g) in dichloromethane (50 ml) at −78° C. under an atmosphere of nitrogen was added, dropwise, boron tribromide (2.26 ml). The reaction was stirred at −10° C. for 2h and then chilled to −78° C. whereupon methanol (5 ml) was added dropwise. The mixture was basified with 2N sodium hydroxide then 2N hydrochloric acid was added to pH 9. The mixture was extracted with dichloromethane (4×50 ml) and the organic phases were combined dried (Na₂SO₄ filtered and concentrated in vacuo to leave a residue which was purified by chromatography using 10% methanol and 1% ammonia in dichloromethane as eluent. The product was dissolved in 5 molar hydrogen chloride in ethyl acetate (15 ml) and methanol (5 ml). The solvent was evaporated to leave a solid which was recrystallised from methanol and ether. The title compound (0.12 g), m.p. 268° C., was collected by filtration and dried under high vacuum. δ(360 MHz, DMSO) 1.86 (3H, s, CH₃), 2.97 (1H, d, J=16.4 Hz, CH$_A$H$_B$—C(CH₃)). 3.14 (1H, dd, J=16.7 and 5.2 Hz, C$\overline{H}_C$—H$_D$—CH$_E$NH), 3.64 (1H, d, J TM 16.7 Hz, $\overline{CH}_C$H$_D$—CH$_E$NH), 3.73 (1H, d, J=CH$_A\overline{H}_B$—C(CH₃)), 5.11 (1H, d, J=5.2 Hz, CH$_C$H$_D$—C$\overline{H}_F$NH), 6.31 (2H, m, CH=C(OH)-CH=CH), 6.65 (1H, d, J=7.8 Hz, C$\overline{H}$=C(OH)-C$\overline{H}$=CH) and 7.15–7.27 (4H, m, aromatics). m/e found: 251.1315. C₁₇H₁₇NO requires: 251.1310. Found: C, 70.0; H, 6.3; N, 4.8. C₁₇H₁₇NO. HCl.O.25 H₂O requires: C, 69.9; H, 6.4; N, 4.8%.

EXAMPLE 14

5,6,11,12-Tetrahydrodibenzo[a,e]cycloocten-6,11-imine hydrochloride

Step A  5-Hydroxyimino-dibenzo[a,e]cyclooctene

To a solution of 5-oxo-dibenzo[a,e]cyclooctene (1 g, Example 1, step E) in ethanol (40 ml) was added hydroxylamine hydrochloride (0.316 g) and pyridine (0.404 ml). This mixture was heated to reflux for 8hr, cooled to room temperature and evaporated to dryness. To the residue was added ethyl acetate (100 ml). water (100 ml),then sodium hydroxide (1M) until pH 10. The aqueous layer was extracted with ethyl acetate (200 ml), the combined organic layers were washed with water (100 ml), brine (100 ml) then dried and evaporated to yield the crude product. Recrystallisation from ethyl acetate-hexane gave pure 5-hydroxyimino-dibenzo[a,e]-cyclooctene (0.72 g, m.p. 191°–192°C.

Step B

13-Hydroxy-5,6,11,12-tetrahydrodibenzo-[a,e]cycloocten-6,11-imine

To a solution of the oxime (step A, 0.25 g) in dry methanol was added methyl orange (3 mg) and sodium cyanoborohydride (0.132 g), followed by dropwise addition of a solution of concentrated hydrochloric acid (250 μl ) in methanol (3 ml). with the pH being maintained between 3–4. After the addition was complete, the mixture was stirred for 2 hours. This addition procedure was repeated three times using a total of 0.53 g sodium cyanoborohydride and 1 ml concentrated hydrochloric acid in methanol (12 ml). After stirring overnight, ethyl acetate (50 ml) and water (50 ml) were added followed by sodium hydroxide (1M) to give pH 14. The aqueous layer was extracted with ethyl acetate (150 ml) and the combined organic layers washed with water (100 ml), brine (100 ml) and then dried and evaporated to yield a mixture of 5-hydroxyl-aminodibenzo[a,e]cyclooctene and 13-hydroxy-5,6,11,12-tetrahydrodibenzo[a,e]cycloocten-6,11-imine. This mixture was heated in xylene (10 ml) at 130° C. for 10 mins, cooled to room temperature and evaporated to yield a crude product which was purified by chromatography (ethyl acetate hexane) to give pure 13-hydroxy-5,6,11,12-tetrahydrodibenzo[a,e]cycloocten-6,11-imine (0.165 g, m.p. 175°–79° C.).

Step C 5,6,11,12-Tetrahydrodibenzo[a,e]cycloocten-6,11-imine hydrochloride

To a solution of the hydroxy imine (step B, 0.165 g) in glacial acetic acid (5 ml) was added zinc powder (0.165 g) and the suspension heated to 60° C. for 8 hours. The mixture was cooled to room temperature and filtered. Sodium hydroxide (1M) was added to the filtrate until pH 12 and the solution was extracted into ethyl acetate (150 ml). The combined organic layers were washed with water (100 ml), brine (100 ml) and then dried and evaporated. The residue was purified using chromatography (methanol-dichloromethane) and treated with saturated hydrogen chloride in ethyl acetate (1 ml) to yield pure 5,6,11,12-tetrahydrodibenzo[a,e]cycloocten-6,11-imine hydrochloride (45 mg, mp>290° C.), δ(DMSO-d₆, 360 MHz) 3.25 (2H, dd, J=16.8 and 5.5 Hz, CH$_A$H$_B$), 3.82 (2H, d, J=16.8 Hz, CH$_A$HB), 5.22 (2H, d, J=5.5 Hz, CH$_C$), 6.92 (4H, s, aromatics), 7.13–7.17 (2H, m, aromatics), 7.24–7.28 (2H. m, aromatics), and 10.17 (2H, bs, NH₂). N.o.e experiments confirmed the structure.

EXAMPLE 15

11-Hydroxy-6-methyl-5,6,11,12-tetrahydrodibenzo[a,e]cycloocten-6,11-imine hydrochloride

Step A

11-Acetoxy-13-hydroxy-6-methyl-5,6,11,12-tetrahydrodibenzo[a,e]cycloocten-6,11-imine To a solution of 13-hydroxy-6-methyl-5,6,11,12tetrahydrodibenzo[a,e]cycloocten-6,11-imine (0.2 g; Example 1, step G) in glacial acetic acid (15 ml) at room temperature was added potassium bromide (20 mg) followed by manganese (III) acetate dihydrate (0.256 g). The mixture was stirred for one hour, ethyl acetate (50 ml) was added, then sodium hydroxide (2M) was added until pH 12. The two layers were separated and the aqueous layer extracted with ethyl acetate (150 ml), the combined organic layers washed with water (100 ml), brine (100 ml), then dried and evaporated. The residue was purified using chromatography (ethyl acetate-hexane) to yield the desired acetate (0.148 g), mp 135°–38° C. (dec).

Step B
11-Hydroxy-6-methyl-5,6,11,12-tetrahydrodibenzo[a,e]cvcloocten-6,11-imine hydrochloride To a solution of the hydroxy imine (step A, 0.14 g) in glacial acetic acid (5 ml) was added zinc powder (0.14 g) and the suspension stirred at 60° C. for 12 hours, then cooled to room temperature and filtered. To the filtrate was added sodium hydroxide (2M) until pH 12 and the solution was extracted with ethyl acetate (150 ml), the combined organic layers washed with water (100 ml), brine (100 ml) then dried and evaporated. Purification of the residue by chromatography (methanol-dichloromethane), followed by treatment with saturated hydrogen chloride in ethyl acetate (2 ml) gave pure 11-hydroxy-6-methyl-5,6,11,12-tetrahydrodibenzo[a,e]cycloocten-6 11-imine hydrochloride (45 mg. mp >280° C.). $\delta$(DMSO-$d_6$, 360 MHz) 1.88 (3H, s, $CH_3$), 3.05 (1H, d, J=16.4 Hz, $CH_eC—CH_AH_B$), 3.27 (1H, d, J=16.0 Hz, $CH_eC—CH_ACH_B$), 3.96 (1H, d, J=16.4 Hz, HO—C—$CH_CH_D$), 4.18 (1H, d, J=16.0 Hz, HO—C—$CH_CH_D$), 6.85–6.94 (4H, m, aromatics), 7.19–7.25 (4H, m, aromatics), 8.39 (1H, bs, OH) and 9.17 and 11.00 (2H, bs, $NH_2$).

EXAMPLE 16
6,11-Dimethyl-5,6,11,12-tetrahydrodibenzo[a,e]cycloocten-6,11-imine hydrochloride

Step A
6-Methyl-13-p-toluenesulphonyl-5,6,11,12-tetrahydrodibenzo[a,e]cycloocten-6,11-imine To a solution of 6-methyl-5,6,11,12-tetrahydrodibenzo[a,e]cycloocten-6,11-imine (Example 1, 2.91 g, 12.4mmol) in dichloromethane (100 ml) was added p-toluenesulphonyl chloride (4.72 g, 24.8mmol) followed by 4-dimethylaminopyridine (3.03 g, 24.8mmol) and the resulting mixture heated at reflux under nitrogen for 14h. The crude reaction mixture was purified by flash chromatography using 50% dichloromethane in petroleum ether (b.pt. 60°–80° C.) as eluent to give the crude product which was triturated with pentane to give the title compound (3.85 g), m.p. 165°–167° C. $\delta$(250 MHz, $CDCl_3$) 1.74 (3H, s, $CH_3$), 2.35 (3H, s, Ar—$CH_3$), 2.88 (1H, d, J=16.0 Hz, $CH_AH_B$), 3.18 (1H, dd, J=4.40 and 16.3 Hz, $CH_CH_D—CH_E$), 4.06 (1H, br d, J=16.1 Hz, $CH_CH_D—CH_E$), 4.16 (1H, d, J=15.9 Hz, $CH_AH_B$) 5.51 (1H, dd, J=2.14 and 4.20 Hz, $CH_CH_D—CH_E$), 6.80–6.92 (5H, m, aromatics), 7.03–7.06 (3H, m, aromatics), 7.18 (2H, d, J=7.95 Hz, aromatics) and 7.68 (2H, d, J=8.35 Hz, aromatics). m/e (EI) 234 (M—$CH_3C_6H_4SO_2$)+; (CI+) 390 (M+1)+.

Step B
6,11-Dimethyl-5,6,11,12-tetrahydrodibenzo[a,e]cycloocten-6,11-imine hydrochloride To a solution of 6-methyl-13-p-toluenesulphonyl-5,6,11,12-tetrahydrodibenzo[a,e]cycloocten-6,11-imine (500 mg) in anhydrous tetrahydrofuran (25 ml) at room temperature and under an atmosphere of nitrogen was added methyllithium (1.7 ml of a 1.6M solution in diethyl ether, 2 molar equivalents) and the resulting mixture was stirred for 7 minutes. The reaction was then quenched with water, diluted with saturated brine and extracted twice with diethyl ether. The combined ethereal extracts were dried over anhydrous sodium sulphate and evaporated. This procedure was then repeated in four separate batches (using 3×900 mg and 1×500 mg to 6-methyl-13-p-toluenesulphonyl-5,6,11,12-tetrahydrodibenzo[a,e]cycloocten-6,11-imine) and all the resulting crude products were combined to give an oil (2.63 g). This was purified by flash chromatography using 2% methanol/0.1% ammonia in dichloromethane as the eluent to give the crude product (355 mg). This was further purified by Lobar chromatography using 4% methanol-0.2% ammonia in dichloromethane as the eluent to give 280 mg of the free base. A portion of this (150 mg) was dissolved in ethyl acetate, filtered and treated with excess hydrogen chloride in diethyl ether which, after evaporation, yielded a product which was recrystallised from methanol/ethyl acetate/diethyl ether to give the title compound as colourless crystals, m.p. 230°–234° C. (sub). $\delta$(250 MHz, $CDCl_3$) 2 23 (6H, s, 2×$CH_3$), 2.90 (2H, d, J=16.4 Hz, 2×$CH_AH_B$), 4.36 (2H, d, J=16.3 Hz, 2×$CH_AH_B$), 6.76–6.79 (2H, m. aromatics), 7.86–6.92 (2H, m, aromatics), 6.97–7.02 (2H, m, aromatics) and 7.09–7.14 (2H, m, aromatics). MS: m/e (EI) 249 (M-HCl)+, 145; (CI+) 250 (M-HCl +1)+, 145; (CI−)248 (M-HCl-1)+, 127. Found: C, 75.01; H, 7.05; N, 4.90. $C_{18}H_{20}ClN.0.15 H_2O$ requires: C, 74.93; H, 7.09; N, 4.85%.

EXAMPLE 17
6-Ethyl-5,6,11,12-tetrahydrodibenzo[a,e]cycloocten-6,11-imine hydrochloride

Step A 5-Hydroxy-5-ethyl-dibenzo[a,e]cyclooctene

To a stirred solution of 5-oxo-dibenzo[a,e]cyclooctene (1.1 g) in anhydrous ether (50 ml) at 0° C. under nitrogen, was added over 10 minutes, a 2.0M solution of ethyl magnesium bromide in tetrahydrofuran (2.5 ml). The mixture was stirred for 30 minutes. then water (20 ml) was added, the solvents were evaporated and the residue extracted with ether, the organic layer washed with water, dried and evaporated to dryness to give the pure alcohol as an oil which crystallised slowly on standing (710 mg). m.p. 81°–85° C.

Step B
6-Ethyl-13-hydroxy-5,6,11,12-tetrahydrodibenzo[a,e]cycloocten-6,11-imine To a suspension of anhydrous sodium acetate (1.15 g) and hydroxylamine hydrochloride (0.97 g) and the preceding alcohol (350 mg) in dichloromethane at reflux was added dichloroacetic acid (2.5 ml) in dichloromethane (15 mg) over 20 minutes with vigorous stirring. The mixture was stirred at reflux for 30 minutes, then cooled and 2M aqueous sodium hydroxide added to pH 12. The organic layer was separated, washed with water and brine, than dried and evaporated. Crystallisation of the residue from n-hexane gave the desired cyclised hydroxylamine (150 mg), m.p. 128°–31°.

Step C
6-Ethyl-5,6,11,12-tetrahydrodibenzo[a,e]cycloocten-6,11-imine hydrochloride To a solution of the N-hydroxy compound from Step B (65 mg) in glacial acetic acid (2 ml) was added zinc dust (250 mg) and the mixture was heated at 65° C. for 90 minutes, then filtered evaporated to dryness and portitioned between ether (10 ml) and 1M aqueous sodium hydroxide (20 ml). The ether layer was washed with water, dried and evaporated and the residue chromatographed on flash silica with 3% methanol/chloroform as eluent. The combined fractions were evaporated to dryness, then dissolved in ethyl acetate and treated with hydrogen chloride in ethyl acetate to give the hydrochloride salt as a buff solid (38.2 g), m.p. 240°–245° C. δ(360 MHz, CDCl$_3$) 1.47 (H, t, J=7.5 Hz, CH$_3$), 2.47 (2H, q, J=7.5 Hz, CH$_2$CH$_3$), 2.88 (1H, d, J=16.2 Hz, C(Et)CH$_A$H$_B$), 3.17 (1H, dd J=16.6 Hz and 5.9 Hz, CHCH$_A$H$_B$), 4.28 (1H, d, J=16.2 Hz, C(Et)-CH$_A$H$_B$) 4.35 (1H, d, J=16.6 Hz, CHCH$_A$H$_B$), 5.41 (1H, t, J=5.9 Hz, CH), 6.80–7.12, (8H, m, aromatics) 10.4 (1H, brs, NH+) and 10.9 (1H, brs, NH+).

EXAMPLE 18

6-Methyl-1-5,6,6a,7,8,9,10,10a,11,12-decahydro[a,e]cyclooctene-6,11-imine hydrochloride A solution of 6-methyl-5,6 11 12-tetrahydrodibenzo[a,e]cycloocten-6,11-imine hydrochloride (100 mg) in glacial acetic acid (5 ml) was hydrogenated for 12h at 50 psi in the presence of platinium oxide catalyst (40 mg). The catalyst was removed by filtration and the solvents evaporated to give the crude product, which was partitioned between 2M aqueous sodium hydroxide (20 ml) and ether (30 ml). The organic extract was washed, dried and evaporated to give the product as the free base. Treatment of this with hydrogen chloride in ethyl acetate followed by trituration with ether, gave the required hydrochloride as a white solid (90 mg), m.p. 230°–3° C.

EXAMPLE 19

6,13-Dimethyl-5,6,11,12-tetrahydrodibenzo[a,e]cycloocten-6,11-imine hydrochloride To a solution of 6-methyl-5,6,11,12-tetrahydrodibenzo[a,e]cycloocten-6,11-imine (0.50 g) in dichloromethane (80 ml) at 0° C. was added methyl iodide (one mole equivalent 0.132 ml). The solution was stirred at room temperature overnight, then a further five mole equivalents of methyl iodide was added. After 4h, the mixture was treated with concentrated ammonia (5 ml), then washed with sodium hydroxide solution, the organic layer removed, dried and evaporated. Crystallisation of the residue gave the N,N-dimethyl quaternary salt (90 mg), m.p. 259°–261° C. Found: C, 58.22; H, 5.59; N, 3.57. C$_{19}$H$_{22}$IN requires C, 58.32; H, 5.67; N, 3.58%). The mother liquors were evaporated and chromatographed on silica gel, eluting with dichloromethane containing 4.5% methanol and 0.5% ammonia to give the N-methyl compound as the free base. Addition of a saturated solution of hydrogen chloride in ethyl acetate to a methanol solution of the free base, followed by evaporation and recrystallisation of the residue from ether-dichloromethane gave the title compound (23 mg). m.p. 272°–273° C. (Found: C, 71.14; H, 6.64; N,4.56. C$_{18}$H$_{19}$N.1.5HCl requires: C, 71.11; H, 6.80; N, 4.60%). m/e : found 249.15080: C$_{18}$H$_{19}$N requires 240.15175.

EXAMPLE 20

Tablet Preparation

Tablets containing 1.0, 2.0, 25.0, 26.0, 50.0 and 100.0 mg, respectively, of the following compounds are prepared as illustrated below:

6-methyl-5,6,11,12-tetrahydrodibenzo[a,e]cycloocten-6,11-imine
3-bromo-6-methyl-5,6,11,12-tetrahydrodibenzo[a,e]cycloocten-6,11-imine
11-hydroxy-6-methyl-5,6,11,12-tetrahydrodibenzo[a,e]cycloocten-6,11-imine
6,11-dimethyl-5,6,11,12-tetrahydrodibenzo[a,e]cycloocten-6,11-imine

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.9 mg, 25.0 mg, 26.0 mg, 50.0 mg and 100.0 mg of active ingredient per tablet.

What is claimed is:

1. A compound of the formula II:

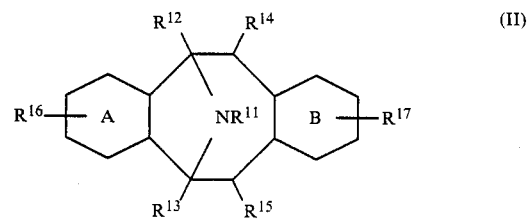

or a salt thereof, wherein rings A and B independently represent cyclohexane or benzene rings; R$^{11}$ is selected from the group consisting of hydrogen and alkyl; and R$^{12}$ to R$^{17}$ independently represent hydrogen, hydroxy, C$_{1-6}$ alkyl, C$_{1-6}$ alkoxy or halogen.

2. The compound of claim 1, wherein rings A and B represent benzene rings and R$^{16}$ and R$^{17}$ independently represent hydrogen, alkyl, hydroxy, methoxy or halogen.

3. The compound of claim 2, wherein R$^{16}$ and R$^{17}$ represent an alkyl selected from the group consisting of methyl, ethyl and butyl or halogen selected from the group consisting of bromo and chloro.

4. The compound of claim 1, wherein R$^{13}$ is an alkyl selected from the group consisting of methyl, ethyl and butyl.

5. The compound of claim 4, wherein said alkyl is methyl.

6. A compound selected from the group consisting of
6-methyl-5,6,11,12-tetrahydrodibenzo[a,e]cycloocten-6,11-imine;
11-n-butyl-6-methyl-5,6,11,12-tetrahydrodibenzo[a,e]cycloocten-6,11-imine;
5,6-dimethyl-5,6,11,12-tetrahydrodibenzo[a,e]cycloocten-6,11-imine;

2-bromo-6-methyl-5,6,11,12-tetrahydrodibenzo[a,e]cycloocten-6,11-imine;
9-bromo-6-methyl-5,6,11,12-tetrahydrodibenzo[a,e]cycloocten-6,11-imine;
3,6-dimethyl-5,6,11,12-tetrahydrodibenzo[a,e]cycloocten-6,11-imine;
6,8-dimethyl-5,6,11,12-tetrahydrodibenzo[a,e]cycloocten-6,11-imine;
2-chloro-6-methyl-5,6,11,12-tetrahydrodibenzo[a,e]cycloocten-6,11-imine;
9-chloro-6-methyl-5,6,11,12-tetrahydrodibenzo[a,e]cycloocten-6,11-imine;
3-bromo-6-methyl-5,6,11,12-tetrahydrodibenzo[a,e]cycloocten-6,11-imine;
6-methyl-5,5,6a-exo,7,8,9,10,10a-exo,11,12-decahydrodibenzo[a,e]cycloocten-6,11-imine;
6-methyl-5,6,6a-endo,7,8,9,10,10a-endo,11,12-decahydrodibenzo[a,e]cycloocten-6,11-imine;
5,6,11,12-tetrahydrodibenzo[a,e]cycloocten-6,11-imine;
6,11-dimethyl-5,6,11,12-tetrahydrodibenzo[a,e]cycloocten-6,11-imine;
2-methoxy-6-methyl-5,6,11,12-tetrahydrodibenzo[a,e]cycloocten-6,11-imine;
3-methoxy-6-methyl-5,6,11,12-tetrahydrodibenzo[a,e]cycloocten-6,11-imine;
2-hydroxy-6-methyl-5,6,11,12-tetrahydrodibenzo[a,e]cycloocten-6,11-imine;
3-hydroxy-6-methyl-5,6,11,12-tetrahydrodibenzo[a,e]cycloocten-6,11-imine;
12-exo-hydroxy-6-methyl-5,6,11,12-tetrahydrodibenzo[a,e]cycloocten-6,11-imine;
1-chloro-6-methyl-5,6,11,12-tetrahydrodibenzo[a,e]cycloocten-6,11-imine;
10-chloro-6-methyl-5,6,11,12-tetrahydrodibenzo[a,e]cycloocten-6,11-imine;
6-ethyl-5,6,11,12-tetrahydrodibenzo[a,e]cycloocten-6,11-imine;
8-bromo-6-methyl-5,6,11,12-tetrahydrodibenzo[a,e]cycloocten-6,11-imine;
11-hydroxy-6-methyl-5,6,11,12-tetrahydrodibenzo[a,e]cycloocten-6,11-imine;
6,13-dimethyl-5,6,11,12-tetrahydrodibenzo[a,e]cycloocten-6,11-imine;
and salts thereof.

7. A pharmaceutical composition for prevention or treatment of neurodegenerative diseases comprising an effective amount of a compound as claimed in claim 1 together with a pharmaceutically acceptable carrier or excipient.

8. A method for the treatment and/or prevention of convulsions which comprises administering to a patient in need of such treatment an effective amount of a compound according to claim 1.

9. A method for the treatment and/or prevention of neurdogenerative diseases which comprises administering to a patient in need of such treatment an effective amount of a compound according to claim 1.

* * * * *